(12) United States Patent
Huizenga et al.

(10) Patent No.: US 11,375,971 B2
(45) Date of Patent: *Jul. 5, 2022

(54) METHOD, SYSTEM, AND COMPUTER PROGRAM PRODUCT FOR DETERMINING A PATIENT RADIATION AND DIAGNOSTIC STUDY SCORE

(71) Applicant: CONVERGENCE MEDICAL, LLC, Dayton, OH (US)

(72) Inventors: James Huizenga, Dayton, OH (US); Brian C. Breneman, Raleigh, NC (US); Kathleen Huizenga, Dayton, OH (US)

(73) Assignee: CLINICENTRIC, LLC, Grand Rapids, MI (US)

( * ) Notice: Subject to any disclaimer, the term of this patent is extended or adjusted under 35 U.S.C. 154(b) by 1011 days.

This patent is subject to a terminal disclaimer.

(21) Appl. No.: 15/984,668

(22) Filed: May 21, 2018

(65) Prior Publication Data

US 2018/0263589 A1    Sep. 20, 2018

Related U.S. Application Data

(63) Continuation of application No. 14/641,463, filed on Mar. 9, 2015, now Pat. No. 9,974,512.

(60) Provisional application No. 61/952,353, filed on Mar. 13, 2014.

(51) Int. Cl.
| | |
|---|---|
| *G01N 33/48* | (2006.01) |
| *G01N 33/50* | (2006.01) |
| *A61B 6/00* | (2006.01) |
| *G16H 50/30* | (2018.01) |
| *G16H 50/20* | (2018.01) |
| *G16Z 99/00* | (2019.01) |
| *G16H 20/40* | (2018.01) |
| *A61B 6/03* | (2006.01) |

(52) U.S. Cl.
CPC ............ *A61B 6/542* (2013.01); *A61B 6/5294* (2013.01); *G16H 20/40* (2018.01); *G16H 50/20* (2018.01); *G16H 50/30* (2018.01); *G16Z 99/00* (2019.02); *A61B 6/032* (2013.01)

(58) Field of Classification Search
CPC ....... A61B 6/542; A61B 6/5294; A61B 6/032; G16H 20/40; G16H 50/30; G16H 50/20
See application file for complete search history.

(56) References Cited

U.S. PATENT DOCUMENTS

| | | |
|---|---|---|
| 4,975,840 A | 12/1990 | DeTore et al. |
| 5,550,734 A | 8/1996 | Tarter et al. |
| 5,583,758 A | 12/1996 | McIlroy et al. |
| 5,679,938 A | 10/1997 | Templeton et al. |
| 5,679,940 A | 10/1997 | Templeton et al. |
| 5,764,923 A | 6/1998 | Tallman et al. |
| 5,809,478 A | 9/1998 | Greco et al. |
| 5,833,599 A | 11/1998 | Schrier et al. |
| 5,867,821 A | 2/1999 | Ballantyne et al. |
| 6,024,699 A | 2/2000 | Surwit et al. |
| 6,088,686 A | 7/2000 | Walker et al. |
| 6,119,103 A | 9/2000 | Basch et al. |
| 6,151,581 A | 11/2000 | Kraftson et al. |
| 6,202,053 B1 | 3/2001 | Christiansen et al. |
| 6,421,650 B1 | 7/2002 | Goetz et al. |
| 6,452,613 B1 | 9/2002 | Lefebvre et al. |
| 6,456,979 B1 | 9/2002 | Flagg |
| 6,484,144 B2 | 11/2002 | Martin et al. |
| 6,533,724 B2 | 3/2003 | McNair |
| 6,647,374 B2 | 11/2003 | Kansal |
| 6,839,690 B1 | 1/2005 | Foth et al. |
| 6,950,807 B2 | 9/2005 | Brock |
| 7,054,758 B2 | 5/2006 | Gill-Garrison et al. |
| 7,097,617 B1 | 7/2006 | Smith |
| 7,107,241 B1 | 9/2006 | Pinto |
| 7,236,952 B1 | 6/2007 | D'Zmura |
| 7,246,740 B2 | 7/2007 | Swift et al. |
| 7,251,625 B2 | 7/2007 | Anglum |
| 7,296,734 B2 | 11/2007 | Pliha |
| 7,306,562 B1 | 12/2007 | Baykal |

(Continued)

OTHER PUBLICATIONS

Mckesson, New McKesson Automation Software Release Enables Advance Analysis for Improved Product Performance, Dec. 3, 2009, McKesson Press Release on Pharmacychoice.com.

(Continued)

*Primary Examiner* — Russell S Negin

(74) *Attorney, Agent, or Firm* — Dawsey Co., LPA; David J. Dawsey

(57) ABSTRACT

A method for determining a patient radiation and diagnostic study score associated with past diagnostic radiologic tests. In light of the obvious benefits of diagnostic radiology, the risks inherent in its use are often overlooked. Ionizing radiation, which is a component of much, but not all, diagnostic radiology, carries with it a small risk of inducing cancer every time it is used. This additional risk, known as "Lifetime Attributable Risk," is layered on top of an individual's lifetime base risk of invasive cancer. The present method for determining a patient radiation and diagnostic study score provides right time, right place, and right format radiology information to assist providers in their medical decision-making. With greater awareness of recent study history, and individually contextualized risk and benefit considerations, providers are more likely to decrease their overall usage of diagnostic radiology and better counsel their patients on future risk.

19 Claims, 23 Drawing Sheets

(56) References Cited

U.S. PATENT DOCUMENTS

| | | |
|---|---|---|
| 7,319,971 B2 | 1/2008 | Abrahams et al. |
| 7,324,954 B2 | 1/2008 | Calderaro et al. |
| 7,343,308 B1 | 3/2008 | Rojewski et al. |
| 7,346,575 B1 | 3/2008 | Ahles et al. |
| 7,386,503 B2 | 6/2008 | Belyi |
| 7,386,506 B2 | 6/2008 | Aoki et al. |
| 7,398,218 B1 | 7/2008 | Bernaski et al. |
| 7,403,922 B1 | 7/2008 | Lewis et al. |
| 7,503,488 B2 | 3/2009 | Davis |
| 7,593,892 B2 | 9/2009 | Balk et al. |
| 7,593,895 B2 | 9/2009 | Belyi |
| 7,620,597 B2 | 11/2009 | Eze |
| 7,630,932 B2 | 12/2009 | Danaher et al. |
| 7,647,263 B2 | 1/2010 | Daul et al. |
| 7,653,555 B2 | 1/2010 | Wiese |
| 7,653,590 B1 | 1/2010 | Kroon et al. |
| 7,653,593 B2 | 1/2010 | Zarikian et al. |
| 7,664,670 B1 | 2/2010 | Weiss |
| 7,668,776 B1 | 2/2010 | Ahles |
| 7,680,719 B1 | 3/2010 | Brady et al. |
| 7,685,000 B1 | 3/2010 | Petit et al. |
| 7,689,494 B2 | 3/2010 | Torre et al. |
| 7,698,157 B2 | 4/2010 | Ghouri |
| 7,698,202 B2 | 4/2010 | Stubbs et al. |
| 7,698,213 B2 | 4/2010 | Lancaster |
| 7,739,256 B2 | 6/2010 | Powell |
| 7,742,982 B2 | 6/2010 | Chaudhuri et al. |
| 7,752,020 B2 | 7/2010 | Seppanen et al. |
| 7,778,856 B2 | 8/2010 | Reynolds et al. |
| 7,778,898 B2 | 8/2010 | Rider et al. |
| 7,783,500 B2 | 8/2010 | Meyer et al. |
| 7,805,353 B2 | 9/2010 | Woodley |
| 7,813,944 B1 | 10/2010 | Luk et al. |
| 7,814,004 B2 | 10/2010 | Haggerty et al. |
| 7,814,008 B2 | 10/2010 | Choudhuri et al. |
| 7,822,670 B2 | 10/2010 | Penello |
| 7,831,494 B2 | 11/2010 | Sloan et al. |
| 7,840,484 B2 | 11/2010 | Haggerty et al. |
| 7,849,004 B2 | 12/2010 | Choudhuri et al. |
| 7,853,520 B2 | 12/2010 | Choudhuri et al. |
| 7,856,388 B1 | 12/2010 | Srivastava et al. |
| 7,860,786 B2 | 12/2010 | Blackburn et al. |
| 9,974,512 B2 * | 5/2018 | Huizenga ............ A61B 6/5294 |
| 2003/0229519 A1 | 12/2003 | Eidex et al. |
| 2005/0228692 A1 | 10/2005 | Hodgdon |
| 2005/0234742 A1 | 10/2005 | Hodgdon |
| 2006/0004701 A1 | 1/2006 | Bacon |
| 2006/0053037 A1 | 3/2006 | Kendall et al. |
| 2006/0080251 A1 | 4/2006 | Fried et al. |
| 2006/0212386 A1 | 9/2006 | Willey et al. |
| 2006/0217824 A1 | 9/2006 | Allmon et al. |
| 2006/0242046 A1 | 10/2006 | Haggerty et al. |
| 2007/0050288 A1 | 3/2007 | Sarkar et al. |
| 2008/0004915 A1 | 1/2008 | Brown |
| 2008/0021803 A1 | 1/2008 | Ahles et al. |
| 2008/0033767 A1 | 2/2008 | Brown |
| 2008/0046268 A1 | 2/2008 | Brown |
| 2008/0086365 A1 | 4/2008 | Zollino et al. |
| 2008/0103834 A1 * | 5/2008 | Reiner ............ A61B 6/5294 705/3 |
| 2008/0133391 A1 | 6/2008 | Kurian et al. |
| 2008/0133402 A1 | 6/2008 | Kurian et al. |
| 2008/0140438 A1 | 6/2008 | Bares |
| 2008/0162383 A1 | 7/2008 | Kraft |
| 2008/0222015 A1 | 9/2008 | Megdal et al. |
| 2008/0222027 A1 | 9/2008 | Megdal et al. |
| 2008/0222038 A1 | 9/2008 | Eden et al. |
| 2008/0228556 A1 | 9/2008 | Megdal et al. |
| 2009/0037323 A1 | 2/2009 | Feinstein et al. |
| 2009/0099959 A1 | 4/2009 | Liao et al. |
| 2009/0106054 A1 | 4/2009 | Sarel |
| 2009/0125319 A1 | 5/2009 | Craine |
| 2009/0171756 A1 | 7/2009 | De Zilwa et al. |
| 2009/0171757 A1 | 7/2009 | Feinstein et al. |
| 2009/0198610 A1 | 8/2009 | Wu et al. |
| 2009/0222308 A1 | 9/2009 | Zoldi et al. |
| 2009/0276233 A1 | 11/2009 | Brimhall et al. |
| 2009/0327120 A1 | 12/2009 | Eze et al. |
| 2010/0010930 A1 | 1/2010 | Allen et al. |
| 2010/0023448 A1 | 1/2010 | Eze |
| 2010/0049539 A1 | 2/2010 | Wiese |
| 2010/0145847 A1 | 6/2010 | Zarikian et al. |
| 2010/0211494 A1 | 8/2010 | Clements |
| 2010/0217738 A1 | 8/2010 | Sarel |
| 2010/0250430 A1 | 9/2010 | Ariff et al. |
| 2010/0268639 A1 | 10/2010 | Feinstein et al. |
| 2010/0274720 A1 | 10/2010 | Carlson et al. |
| 2010/0305993 A1 | 12/2010 | Fisher |
| 2011/0144024 A1 * | 6/2011 | Petersen ............ A61P 39/06 514/13.7 |
| 2011/0238593 A1 | 9/2011 | Hearnes, II et al. |
| 2011/0288886 A1 | 11/2011 | Whiddon et al. |

OTHER PUBLICATIONS

Mckesson, McKesson Automation Decision Support, McKesson Automation Decision Support Overview Brochure.

Brenner et al. Computed Tomography—An increasing source of radiation exposure. The New England Journal of Medicine, vol. 357, 2007, pp. 2277-2284.

Godar et al. Solar UV doses of young Americans and vitamin D3 production Environmental Health Perspectives, vol. 120, Jan. 2012, pp. 139-143.

* cited by examiner

Figure 1 – Database (100) Record of Patient A

| Patient ID | Date of Birth | Date of Service | Test |
|---|---|---|---|
| A | 12/27/65 | 1/2/96 | 1 |
| A | 12/27/65 | 2/4/96 | 2 |
| A | 12/27/65 | 3/3/97 | 1 |
| A | 12/27/65 | 4/16/99 | 1 |
| A | 12/27/65 | 4/16/99 | 2 |
| A | 12/27/65 | 4/16/99 | 3 |
| A | 12/27/65 | 4/16/99 | 4 |
| A | 12/27/65 | 4/16/99 | 5 |
| A | 12/27/65 | 5/17/01 | 1 |
| A | 12/27/65 | 2/20/04 | 4 |
| A | 12/27/65 | 2/20/04 | 5 |
| A | 12/27/65 | 8/23/07 | 1 |
| A | 12/27/65 | 8/24/07 | 1 |
| A | 12/27/65 | 11/12/10 | 1 |
| A | 12/27/65 | 11/12/10 | 2 |
| A | 12/27/65 | 11/12/10 | 3 |
| A | 12/27/65 | 11/12/10 | 4 |
| A | 12/27/65 | 11/12/10 | 5 |
| A | 12/27/65 | 5/30/13 | 1 |
| A | 12/27/65 | 5/30/13 | 2 |

Figure 2 – Radiation Dose in mSv for each Radiologic Test (200)

| Radiologic Test (200) | mSv |
|---|---|
| 1 | 0.1 |
| 2 | 1 |
| 3 | 5 |
| 4 | 20 |
| 5 | 0 |

Figure 3 – Age Adjustment Factor (300)

| Age | Age Adjustment Factor (300) |
|---|---|
| 0.00 | 3 |
| 1.00 | 2.92 |
| 2.00 | 2.84 |
| 3.00 | 2.76 |
| 4.00 | 2.68 |
| 5.00 | 2.6 |
| 6.00 | 2.52 |
| 7.00 | 2.44 |
| 8.00 | 2.36 |
| 9.00 | 2.28 |
| 10.00 | 2.2 |
| 11.00 | 2.12 |
| 12.00 | 2.04 |
| 13.00 | 1.96 |
| 14.00 | 1.88 |
| 15.00 | 1.8 |
| 16.00 | 1.72 |
| 17.00 | 1.64 |
| 18.00 | 1.56 |
| 19.00 | 1.48 |
| 20.00 | 1.4 |
| 21.00 | 1.32 |
| 22.00 | 1.24 |
| 23.00 | 1.16 |
| 24.00 | 1.08 |
| 25.00+ | 1 |

Figure 4 – Patient A with appended mSv, Age Adjustment Factor (300), and Lifetime Attributable Risk (400)

| Patient ID | Date of Birth | Date of Service | Radiologic Test (200) | mSv | AAF (300) | LAR (400) (%) |
|---|---|---|---|---|---|---|
| A | 12/27/65 | 1/2/72 | 1 | 0.1 | 2.52 | 0.00252 |
| A | 12/27/65 | 2/4/78 | 2 | 1 | 2.03 | 0.0203 |
| A | 12/27/65 | 3/3/80 | 1 | 0.1 | 1.86 | 0.00186 |
| A | 12/27/65 | 4/16/90 | 1 | 0.1 | 1.05 | 0.00105 |
| A | 12/27/65 | 4/17/90 | 2 | 1 | 1.05 | 0.0105 |
| A | 12/27/65 | 4/18/90 | 3 | 5 | 1.05 | 0.0525 |
| A | 12/27/65 | 4/19/90 | 4 | 20 | 1.05 | 0.21 |
| A | 12/27/65 | 4/20/90 | 5 | 0 | 1.05 | 0 |
| A | 12/27/65 | 5/17/01 | 1 | 0.1 | 1 | 0.001 |
| A | 12/27/65 | 2/20/04 | 4 | 20 | 1 | 0.2 |
| A | 12/27/65 | 2/20/04 | 5 | 0 | 1 | 0 |
| A | 12/27/65 | 8/23/07 | 1 | 0.1 | 1 | 0.001 |
| A | 12/27/65 | 8/24/07 | 1 | 0.1 | 1 | 0.001 |
| A | 12/27/65 | 11/12/10 | 1 | 0.1 | 1 | 0.001 |
| A | 12/27/65 | 11/12/10 | 2 | 1 | 1 | 0.01 |
| A | 12/27/65 | 11/12/10 | 3 | 5 | 1 | 0.05 |
| A | 12/27/65 | 11/12/10 | 4 | 20 | 1 | 0.2 |
| A | 12/27/65 | 11/12/10 | 5 | 0 | 1 | 0 |
| A | 12/27/65 | 5/30/13 | 1 | 0.1 | 1 | 0.001 |
| A | 12/27/65 | 5/30/13 | 2 | 1 | 1 | 0.01 |
| | | | | | Total LAR (400) | 0.77373 |

Figure 5 – Population Lifetime Attributable Risk (400) Values

| Patient ID | LAR (400) (%) |
|:---:|:---:|
| C | 0.1 |
| D | 0.15 |
| Q | 0.18 |
| V | 0.19 |
| W | 0.19 |
| E | 0.2 |
| R | 0.2 |
| X | 0.24 |
| T | 0.28 |
| P | 0.29 |
| S | 0.33 |
| M | 0.34 |
| Y | 0.39 |
| L | 0.45 |
| K | 0.49 |
| U | 0.54 |
| I | 0.6 |
| O | 0.73 |
| A | 0.77 |
| N | 0.84 |
| J | 0.87 |
| B | 1 |
| H | 1.8 |
| G | 2.4 |
| F | 4.4 |

Figure 6 – Example Scaled Lifetime Attributable Risk (410) Value Computation

| Patient ID | Total LAR (400) (%) | % Contribution | Running total | Scaled Lifetime Attributable Risk (410) |
|---|---|---|---|---|
| C | 0.1 | 0.005376344 | 0.005376344 | 1 |
| D | 0.15 | 0.008064516 | 0.01344086 | 1 |
| Q | 0.18 | 0.009677419 | 0.02311828 | 2 |
| V | 0.19 | 0.010215054 | 0.033333333 | 3 |
| W | 0.19 | 0.010215054 | 0.043548387 | 4 |
| E | 0.2 | 0.010752688 | 0.054301075 | 5 |
| R | 0.2 | 0.010752688 | 0.065053763 | 7 |
| X | 0.24 | 0.012903226 | 0.077956989 | 8 |
| T | 0.28 | 0.015053763 | 0.093010753 | 9 |
| P | 0.29 | 0.015591398 | 0.108602151 | 11 |
| S | 0.33 | 0.017741935 | 0.126344086 | 13 |
| M | 0.34 | 0.01827957 | 0.144623656 | 14 |
| Y | 0.39 | 0.020967742 | 0.165591398 | 17 |
| L | 0.45 | 0.024193548 | 0.189784946 | 19 |
| K | 0.49 | 0.026344086 | 0.216129032 | 22 |
| U | 0.54 | 0.029032258 | 0.24516129 | 25 |
| I | 0.6 | 0.032258065 | 0.316666667 | 32 |
| O | 0.73 | 0.039247312 | 0.284408602 | 28 |
| A | 0.77 | 0.041397849 | 0.358064516 | 36 |
| N | 0.84 | 0.04516129 | 0.403225806 | 40 |
| J | 0.87 | 0.046774194 | 0.45 | 45 |
| B | 1 | 0.053763441 | 0.503763441 | 50 |
| H | 1.8 | 0.096774194 | 0.600537634 | 60 |
| G | 2.9 | 0.155913978 | 0.756451613 | 76 |
| F | 4.53 | 0.243548387 | 1 | 99 |
|   | 18.6 |   |   |   |

Figure 7 – Example Radiation and Diagnostic Study Score (10) with Recent Study Indicator (500)

| Patient ID | Scaled Lifetime Attributable Risk (410) | Recent Study Indicator (500) | Composite Radiation and Diagnostic Study Score (10) with Recent Study Indicator (500) |
| --- | --- | --- | --- |
| C | 1 | 0 | 010 |
| D | 1 | 0 | 010 |
| Q | 2 | 3 | 023 |
| V | 3 | 0 | 040 |
| W | 4 | 0 | 050 |
| E | 5 | 1 | 061 |
| R | 7 | 1 | 071 |
| X | 8 | 5 | 085 |
| T | 9 | 3 | 093 |
| P | 11 | 0 | 110 |
| S | 13 | 0 | 130 |
| M | 14 | 0 | 140 |
| Y | 17 | 0 | 170 |
| L | 19 | 0 | 190 |
| K | 22 | 3 | 223 |
| U | 25 | 1 | 251 |
| I | 32 | 1 | 321 |
| O | 28 | 1 | 281 |
| A | 36 | 0 | 360 |
| N | 40 | 13 | 409 |
| J | 45 | 0 | 450 |
| B | 50 | 2 | 502 |
| H | 60 | 5 | 605 |
| G | 76 | 3 | 763 |
| F | 99 | 0 | 990 |

Figure 8 - Example Previous Study Factor (800)

| Repetitive Test Number (810) | Previous Study Factor (800) |
|:---:|:---:|
| 1 | 1 |
| 2 | 1.69 |
| 3 | 2.1 |
| 4 | 2.39 |
| 5 | 2.61 |
| 6 | 2.79 |
| 7 | 2.95 |
| 8 | 3.08 |
| 9 | 3.2 |
| 10 | 3.3 |
| 11 | 3.4 |
| 12 | 3.48 |
| 13 | 3.56 |
| 14 | 3.64 |
| 15 | 3.71 |
| 16 | 3.77 |
| 17 | 3.83 |
| 18 | 3.89 |
| 19 | 3.94 |
| 20 | 4 |

Figure 9 – Example Time Decay Element (900) for Twenty 10 Day Increments

| Days Elapsed | Time Decay Element (900) |
|---|---|
| 1 | 0.999 |
| 10 | 0.99 |
| 20 | 0.98 |
| 30 | 0.97 |
| 40 | 0.961 |
| 50 | 0.951 |
| 60 | 0.942 |
| 70 | 0.932 |
| 80 | 0.923 |
| 90 | 0.914 |
| 100 | 0.905 |
| 110 | 0.896 |
| 120 | 0.887 |
| 130 | 0.878 |
| 140 | 0.869 |
| 150 | 0.861 |
| 160 | 0.852 |
| 170 | 0.844 |
| 180 | 0.835 |
| 190 | 0.827 |

Figure 10 – Usage Metric Calculation for Patient A

| Patient ID | Date of Birth | Date of Service | Test | Previous Study Factor (800) | Time Decay Element (900) | Usage Metric (1000) |
|---|---|---|---|---|---|---|
| A | 12/27/65 | 1/2/72 | 1 | 1 | 2.68191E-07 | 2.68191E-07 |
| A | 12/27/65 | 2/4/78 | 2 | 1 | 2.48446E-06 | 2.48446E-06 |
| A | 12/27/65 | 3/3/80 | 1 | 1.69 | 5.30387E-06 | 8.96353E-06 |
| A | 12/27/65 | 4/16/90 | 1 | 2.1 | 0.000214066 | 0.000449539 |
| A | 12/27/65 | 4/17/90 | 2 | 1.69 | 0.00021428 | 0.000362134 |
| A | 12/27/65 | 4/18/90 | 3 | 1 | 0.000214495 | 0.000214495 |
| A | 12/27/65 | 4/19/90 | 4 | 1 | 0.00021471 | 0.00021471 |
| A | 12/27/65 | 4/20/90 | 5 | 1 | 0.000214925 | 0.000214925 |
| A | 12/27/65 | 5/17/01 | 1 | 2.39 | 0.012299466 | 0.029395723 |
| A | 12/27/65 | 2/20/04 | 4 | 1.69 | 0.033752708 | 0.057042076 |
| A | 12/27/65 | 2/20/04 | 5 | 1.69 | 0.033752708 | 0.057042076 |
| A | 12/27/65 | 8/23/07 | 1 | 2.61 | 0.121474101 | 0.317047403 |
| A | 12/27/65 | 8/24/07 | 1 | 2.79 | 0.121595696 | 0.339251993 |
| A | 12/27/65 | 11/12/10 | 1 | 2.95 | 0.394370163 | 1.163391981 |
| A | 12/27/65 | 11/12/10 | 2 | 2.1 | 0.394370163 | 0.828177343 |
| A | 12/27/65 | 11/12/10 | 3 | 1.69 | 0.394370163 | 0.666485576 |
| A | 12/27/65 | 11/12/10 | 4 | 2.1 | 0.394370163 | 0.828177343 |
| A | 12/27/65 | 11/12/10 | 5 | 2.1 | 0.394370163 | 0.828177343 |
| A | 12/27/65 | 5/30/13 | 1 | 3.08 | 1 | 3.08 |
| A | 12/27/65 | 5/30/13 | 2 | 2.61 | 1 | 2.61 |
| | | | | | Total Usage Metric (1000) | 10.80565637 |

| Patientid | DOB | Age | Service Date | CPT Code | CPT Mod | Prov ID | Prov Type | Rev Code | CPT Descriptor |
|---|---|---|---|---|---|---|---|---|---|
| 1234 | 1/7/99 | 11.1 | 2/2/10 | 71010 | | 1 | MD | NA | X-ray of chest: frontal view |
| 1234 | 1/7/99 | 11.4 | 5/17/10 | 74020 | | 2 | HO | 320 | X-ray of abdomen with erect views |
| 1234 | 1/7/99 | 11.4 | 5/17/10 | 74020 | 26 | 3 | PG | NA | X-ray of abdomen with erect views |
| 1234 | 1/7/99 | 11.4 | 5/17/10 | 74022 | 26 | 3 | PG | NA | X-ray of abdomen with supine... |
| 1234 | 1/7/99 | 11.7 | 9/10/10 | 73100 | 26 | 3 | PG | NA | X-ray of wrist |
| 1234 | 1/7/99 | 11.7 | 9/14/10 | 73100 | 26 | 3 | PG | NA | X-ray of wrist |
| 1234 | 1/7/99 | 11.7 | 9/14/10 | 73100 | RT | 2 | HO | 320 | X-ray of wrist |
| 1234 | 1/7/99 | 12.2 | 3/17/11 | 73562 | 26 | 3 | PG | NA | X-ray of knee |
| 1234 | 1/7/99 | 12.9 | 11/15/11 | 70450 | | 2 | HO | 351 | CT of head or brain |
| 1234 | 1/7/99 | 12.9 | 11/15/11 | 70450 | | 2 | HO | 351 | CT of head or brain |
| 1234 | 1/7/99 | 12.9 | 11/15/11 | 70450 | 26 | 3 | PG | NA | CT of head or brain |
| 1234 | 1/7/99 | 13.8 | 10/12/12 | 73620 | LT | 4 | DP | NA | X-ray of foot |
| 1234 | 1/7/99 | 13.8 | 10/12/12 | 73620 | RT | 4 | DP | NA | X-ray of foot |
| 1234 | 1/7/99 | 13.9 | 12/18/12 | 70551 | | 2 | HO | 611 | MRI of brain |
| 1234 | 1/7/99 | 13.9 | 12/18/12 | 70551 | 26 | 3 | PG | NA | MRI of brain |
| 1234 | 1/7/99 | 14.1 | 1/30/13 | 76882 | 26 | 3 | PG | NA | Real time nonvascular ultra... |
| 1234 | 1/7/99 | 14.3 | 4/16/13 | 73630 | | 2 | HO | 320 | X-ray of foot |
| 1234 | 1/7/99 | 14.3 | 4/16/13 | 73630 | 26 | 3 | PG | NA | X-ray of foot |

Figure 15 – Example Patient Record of Radiologic Tests (200)

| Type | Study | mSv |
|---|---|---|
| pl | skull | 0.1 |
| pl | c-spine | 0.2 |
| pl | t-spine | 1 |
| pl | l-spine | 1.5 |
| pl | pa lat chest | 0.1 |
| pl | shoulder | 0.01 |
| pl | knee | 0.005 |
| ct | head | 2 |
| ct | neck | 3 |
| ct | abd | 8 |
| ct | pelvis | 6 |
| ct | 3 phase liver | 15 |
| ct | spine | 6 |
| ct | coronary angiography | 16 |
| fl | thoracic angio | 5 |
| fl | abdominal angio | 12 |
| fl | TIPS | 70 |
| fl | Pelvic vein embolization | 60 |
| fl | Upper GI series w/ fluoro | 6 |
| fl | Small Bowel Series | 5 |
| fl | Barium enema w/ fluoro | 8 |
| fl | ERCP | 4 |
| nm | Thyroid Na I 123 | 1.9 |
| nm | Thyroid 99mTc-pertechnet | 4.8 |
| nm | parathyroid | 6.7 |
| nm | Cardiac Stress thallium 201 | 40.7 |
| mr | | 0 |
| us | | 0 |

Figure 16 – Example Radiation Dose in mSv for Additional Radiologic Tests (200)

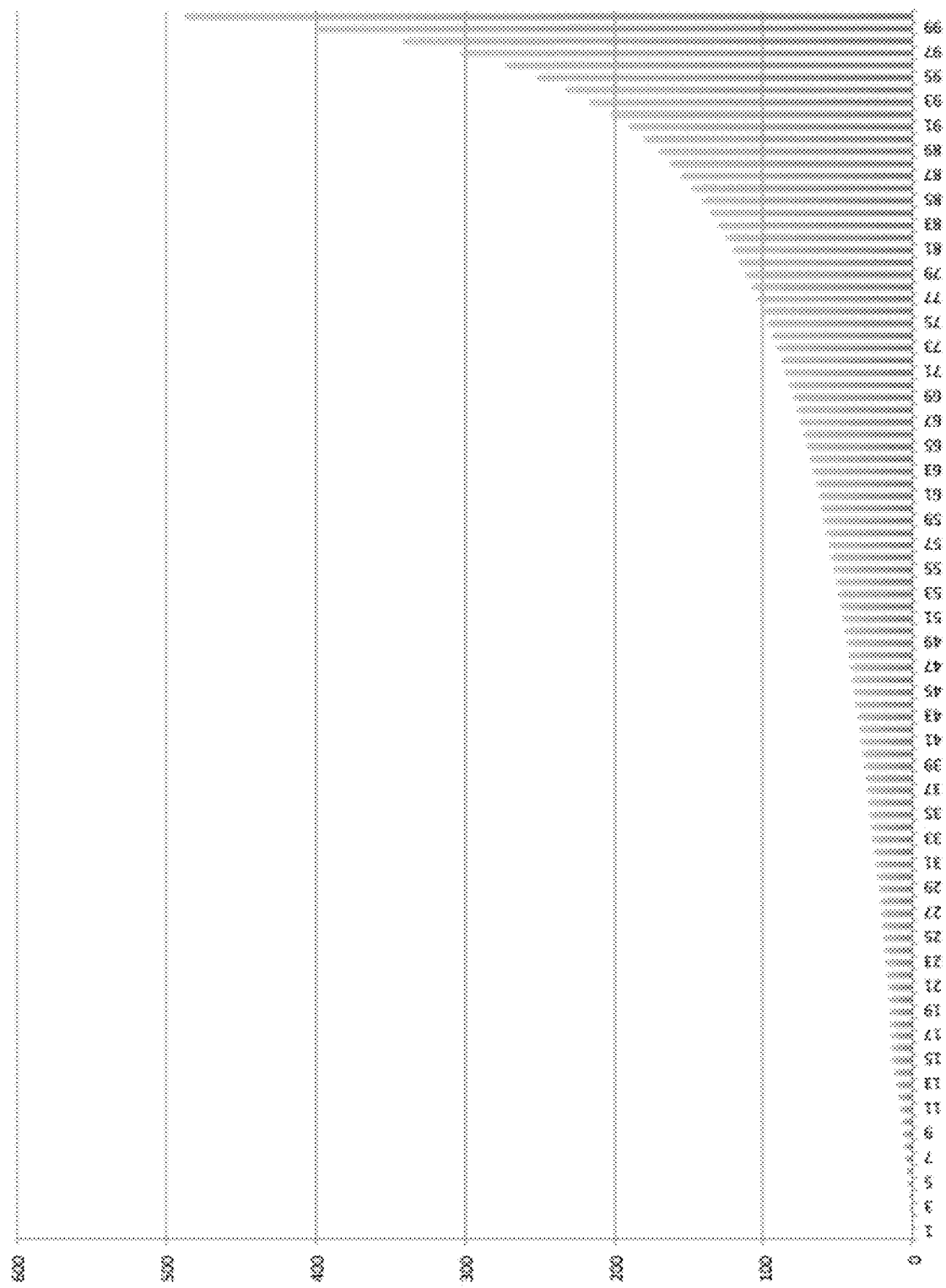
Figure 17 – Example Graph of General Population Total Lifetime Attributable Risk vs. Scaled Value for Risk

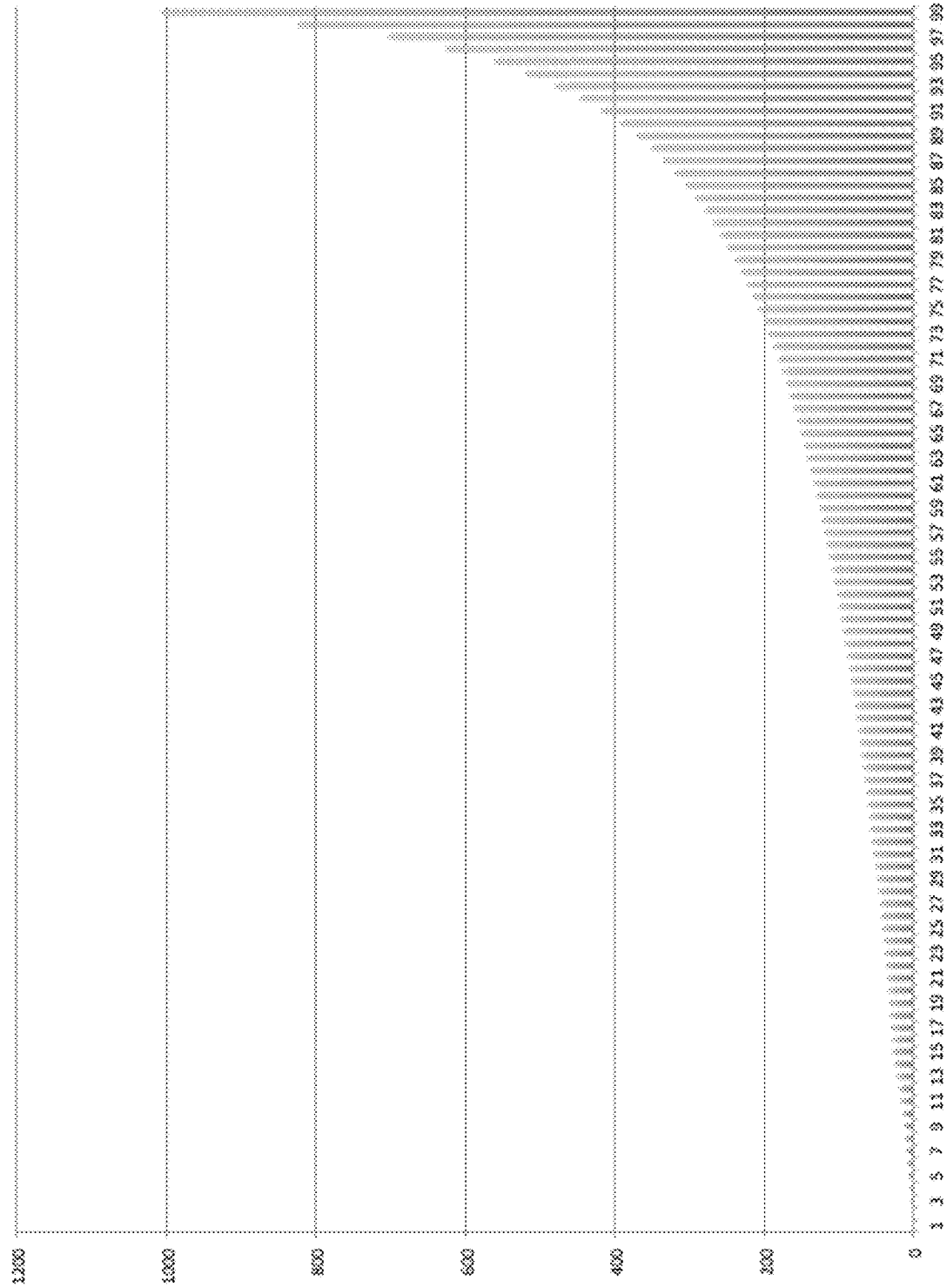
Figure 18 – Example Graph of General Population Total Lifetime Attributable Risk vs. Scaled Value for Risk Adjusted to 50 = 1% (note: Lifetime Attributable Risk units / 100 = %)

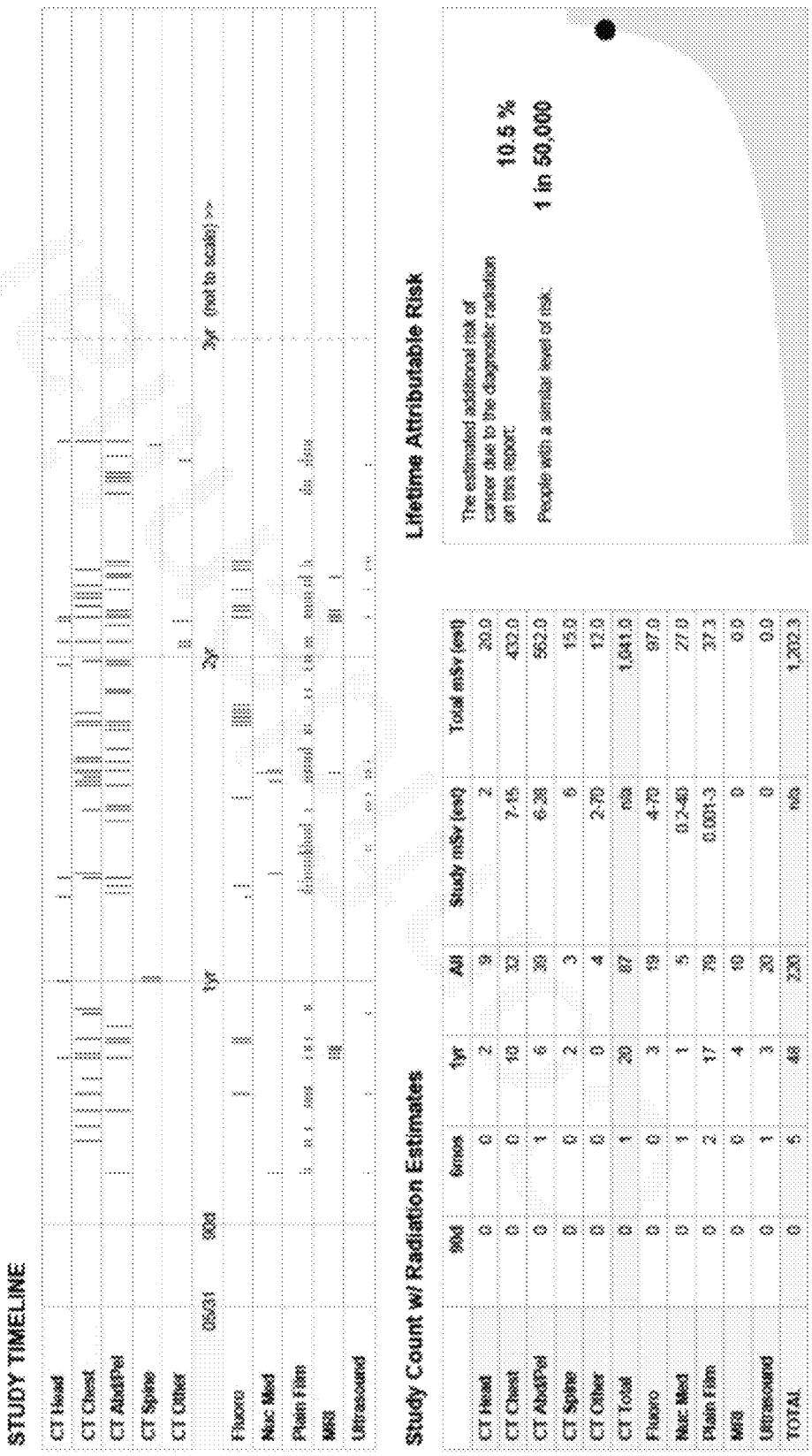
Figure 19 – Example Front Page of Report (700)

Rads Report Layout

This report represents a reconstructed radiology timeline based on aggregating multiple sources of data. Note that because of billing discrepancies, demographic discrepancies, and other possible differences in data, this report should be treated only as an estimate.

The Study Timeline diagrams the general types of studies performed and their service dates along a proportional timeline for 3 years, and non-proportional thereafter. In some cases, the number of studies limits proportional spacing.

Red hash marks | indicate studies that use ionizing radiation. The height of the hash mark provides a general indication of relative radiation exposure.

Rads Check uses the same average radiation exposure for the same study type regardless of the machine used for imaging. In reality, doses vary across machines and across protocols.

Rads Score

The Rads Score is intended to raise awareness to the amount and type of radiology information on the report. A higher score equates to more available information and higher accumulated risk due to radiation exposure.

Approximately 1-2% of the population has a score of 500 or more.

Using accepted risk calculation strategies a score of 500 correlates to a 1% increased lifetime risk of cancer above a patient's baseline risk. Note that at baseline, humans have a lifetime risk of invasive cancer of approximately 37.5% for women and 44.9% for men.

The Rads Score is non-linear and increases rapidly above a score of 500 such that at 950, a patient's additional lifetime risk of cancer is approximately 10% (or more).

The third digit of the Rads Score equates to the number of CT studies within the last year + any other study in the last 90 days. The maximum number displayed is "9". The study count section of the report can be used for further assessment.

How should this report be used?

1. This report is intended to promote discussion and thought about the risks and benefits of diagnostic radiation. In the vast majority of cases, the benefits of diagnostic radiation far outweigh the risks.

2. This report contains information available from multiple sources. There is always the possibility that some information is missing from this report. Additional information will usually add to the risk estimates and as such, the Rads Report should be considered to represent the minimum risk equation.

3. In some cases, cumulative radiation exposure and knowledge of recent testing may impact additional diagnostic imaging choices. In all cases it is up to the provider and the patient to assess and apply the risks and benefits of additional testing.

Figure 20 – Example Rear Page of Report (700)

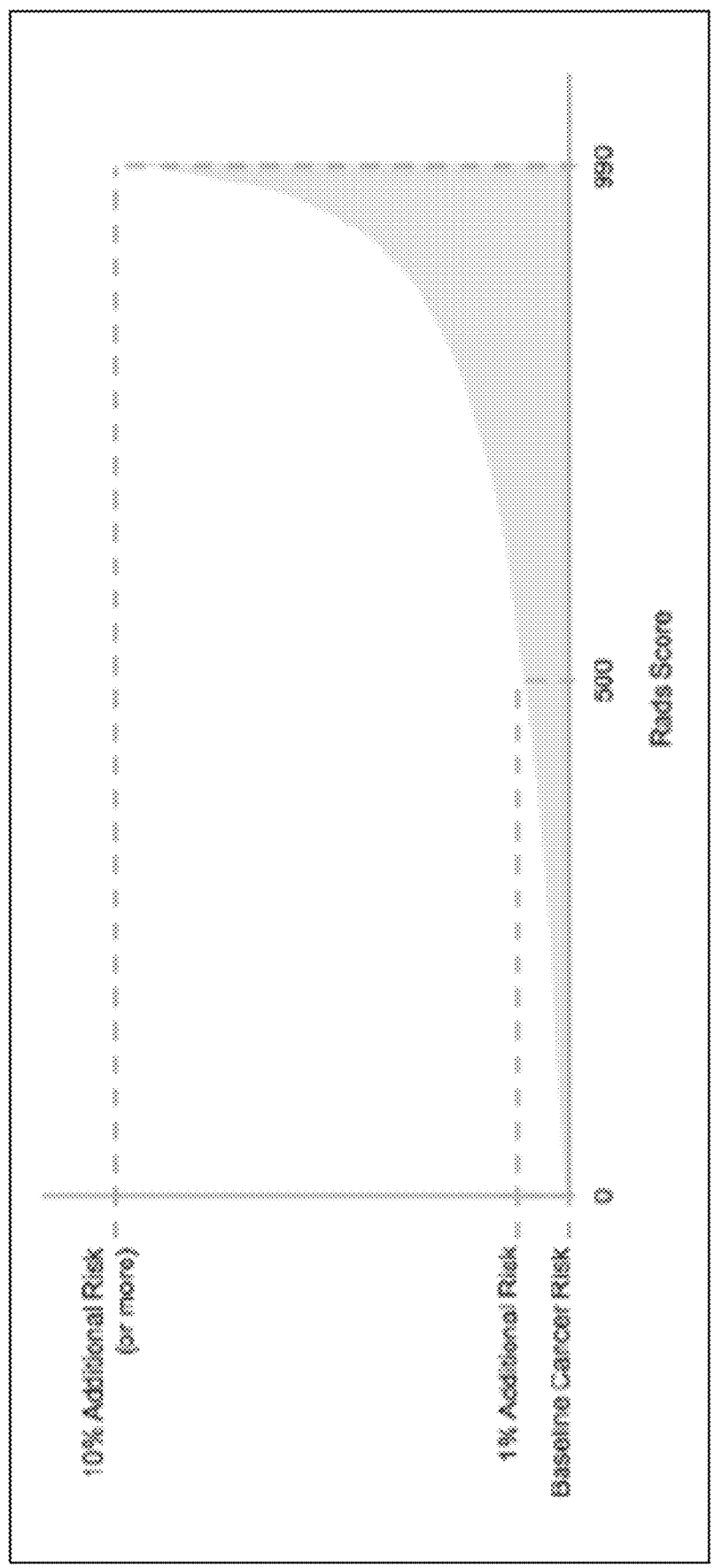
Figure 21 – Example Rear Page of Report (700)

Figure 22 – Resolution Metric Calculation for Patient A

| Patient ID | Date of Birth | Date of Service | Radiologic Test (200) | Resolution Metric (1100) |
|---|---|---|---|---|
| A | 12/27/65 | 1/2/72 | 1 | 0.1 |
| A | 12/27/65 | 2/4/78 | 2 | 1 |
| A | 12/27/65 | 3/3/80 | 1 | 0.1 |
| A | 12/27/65 | 4/16/90 | 1 | 0.1 |
| A | 12/27/65 | 4/17/90 | 2 | 1 |
| A | 12/27/65 | 4/18/90 | 3 | 5 |
| A | 12/27/65 | 4/19/90 | 4 | 20 |
| A | 12/27/65 | 4/20/90 | 5 | 20 |
| A | 12/27/65 | 5/17/01 | 1 | 0.1 |
| A | 12/27/65 | 2/20/04 | 4 | 20 |
| A | 12/27/65 | 2/20/04 | 5 | 20 |
| A | 12/27/65 | 8/23/07 | 1 | 0.1 |
| A | 12/27/65 | 8/24/07 | 1 | 0.1 |
| A | 12/27/65 | 11/12/10 | 1 | 0.1 |
| A | 12/27/65 | 11/12/10 | 2 | 1 |
| A | 12/27/65 | 11/12/10 | 3 | 5 |
| A | 12/27/65 | 11/12/10 | 4 | 20 |
| A | 12/27/65 | 11/12/10 | 5 | 20 |
| A | 12/27/65 | 5/30/13 | 1 | 0.1 |
| A | 12/27/65 | 5/30/13 | 2 | 1 |
| | | | | |
| | | | Total Resolution Metric (1100) | 134.8 |

METHOD, SYSTEM, AND COMPUTER PROGRAM PRODUCT FOR DETERMINING A PATIENT RADIATION AND DIAGNOSTIC STUDY SCORE

CROSS-REFERENCE TO RELATED APPLICATIONS

This application is a continuation of U.S. patent application Ser. No. 14/641,463, filed on Mar. 9, 2015, which claims the benefit of U.S. provisional patent application Ser. No. 61/952,353, filed on Mar. 13, 2014, all of which is incorporated by reference as if completely written herein.

STATEMENT REGARDING FEDERALLY SPONSORED RESEARCH OR DEVELOPMENT

This invention was not made as part of a federally sponsored research or development project.

TECHNICAL FIELD

The present invention relates to the assessment of risk secondary to ionizing radiation exposure as it relates to its use in the medical field.

BACKGROUND OF THE INVENTION

The use of diagnostic radiology has been dramatically increasing for many years with proportional financial and patient safety effects. Between 2000 and 2007 the use of imaging studies grew faster than that of any other physician service in the Medicare population. Currently, there are more than 70 million CT scans performed in the United States every year. A study by the influential group America's Health Insurance Plans claims that 20% to 50% of all "high-tech" imaging provides no useful information and may be unnecessary, and the radiation exposure from these scans may lead to thousands of cancer-related deaths. Reports like these have led to cost and safety concerns among key federal agencies like the Congressional Budget Office, Government Accountability Office, and Medicare Payment Advisory Commission, and steps have been taken in recent years to reduce reimbursements for imaging as one means of reducing overall usage and exposure.

The overuse of diagnostic radiology is partially explained by the fact that it has been enormously helpful in the areas of non-invasive diagnosis. Some conditions that previously required general surgery to diagnose can now be painlessly and quickly found with a CT Scan, with much less inherent risk to the patient. The diagnostic radiology field is also responsible for saving many patients' lives by facilitating the timely diagnosis of dangerous medical conditions, such as internal bleeding. As a result of these obvious benefits of diagnostic radiology, the risks inherent in its use are often overlooked. Ionizing radiation, which is a component of much (but not all) diagnostic radiology, carries with it a small risk of inducing cancer every time it is used. This additional risk is known as "Lifetime Attributable Risk" or "LAR". The LAR due to medical imaging is layered on top of an individual's lifetime base risk of invasive cancer, which is approximately 37% for women and 45% for men.

The LAR due to diagnostic radiology has historically been assumed to be relatively low, and usually less than 1%, but a sub-group of individuals in society exists with a much higher LAR. This sub-group represents approximately 2% of the population as found in the large study population used to develop the Rads Scoring system. Although this group of individuals is numerically small, they account for 25% of all the CT Scans in the study group. This finding conforms with the general understanding that the top 1% of medical users consume about 20% of the resources and the top 5% consume nearly 50%. In the case of radiology overuse, the top 2% of patient consumers are also absorbing much of the additional cancer risk for the population. In many cases, this additional cancer risk approaches 10% and in rare cases, the additional risk approaches 20%.

The above begs the question, if radiology overuse is an accepted problem that results in financial waste and patient risk with often times little benefit, why does it continue? There are several possible answers. Firstly, medico-legal concerns amongst providers are generally accepted to be a source of defensive medicine practice patterns with resultant overuse of diagnostics of all types, including radiology. Secondly, patient satisfaction leads many institutions down the path of giving patients what they want, be it x-rays, antibiotics, or pain medications. The Federal Government's incorporation of patient satisfaction into reimbursement equations creates direct financial incentives to make patients happy, even when it may not be in their overall best interest. Thirdly, hidden or difficult-to-get-to information leads to repeat diagnostics when it becomes easier to order it again rather than find and access previous results. Lastly, there are many times a provider will order a test without knowledge of recent testing that may have otherwise dissuaded them from ordering additional tests.

There are of course many more possible reasons behind the overuse of diagnostic radiology, but a common thread emerges in the above. Our current healthcare system provides many more reasons to order a radiologic test as compared with reasons to not order a radiologic test. At least one component of the solution to the problem of radiology overuse must therefore involve the creation of a reason (or reasons) not to order radiological tests. Some of these reasons could be (a) increasing awareness of previous testing, (b) increasing awareness of additional radiation risk exposure for the patient, (c) instituting checks and balances when ordering additional studies for high risk patients, (d) exposure to financial risk for inappropriate ordering, and (e) medico-legal exposure for unnecessary testing that impacts patient safety.

One additional problem with radiology overuse is that even when it is suspected, many providers lack the ability to properly contextualize the amount of overuse and apply it to a risk/benefit analysis. Therefore, clinical decisions are often made without a true understanding of accumulated risk. In a similar vein, discussions with patients about radiology overuse are often lacking in content and relevancy, or worse, contaminated with misinformation. Therefore, an additional component of any solution must be the creation of relevant and contextual information for a provider and patient to consider. In order for this information to be relevant and contextual, it must relate to identifiable, "down to earth", quantities and concepts.

The present method, system, and computer program product for determining a patient Radiation and Diagnostic Study Score provides right time, right place, and right format radiology information to providers to assist them in their medical decision-making. With greater awareness of recent study history, and individually contextualized risk and benefit considerations, providers are more likely to decrease their overall usage of diagnostic radiology, and also be enabled to better counsel their patients on future risk.

SUMMARY OF THE INVENTION

A method for determining a patient radiation and diagnostic study score associated with past diagnostic radiologic tests. In light of the obvious benefits of diagnostic radiology, the risks inherent in its use are often overlooked. Ionizing radiation, which is a component of much, but not all, diagnostic radiology, carries with it a small risk of inducing cancer every time it is used. This additional risk, known as "Lifetime Attributable Risk," is layered on top of an individual's lifetime base risk of invasive cancer. The present method for determining a patient radiation and diagnostic study score provides right time, right place, and right format radiology information to assist providers in their medical decision-making. With greater awareness of recent study history, and individually contextualized risk and benefit considerations, providers are more likely to decrease their overall usage of diagnostic radiology and better counsel their patients on future risk.

BRIEF DESCRIPTION OF THE DRAWINGS

Without limiting the scope of the present method, system, and program, referring now to the drawings and figures:

FIG. 1 shows an illustrative table showing a hypothetical database record of a patient, in accordance with an embodiment of the invention;

FIG. 2 shows an illustrative table showing a hypothetical correlation between radiologic tests and a measure of ionizing radiation, in accordance with an embodiment of the invention;

FIG. 3 shows an illustrative table showing a hypothetical correlation between age and an age adjustment factor, in accordance with an embodiment of the invention;

FIG. 4 shows an illustrative table showing a hypothetical patient record with a measure of ionizing radiation in mSv, an Age Adjustment Factor, a Test Specific Lifetime Attributable Risk, and a Total Lifetime Attributable Risk, in accordance with an embodiment of the invention;

FIG. 5 shows an illustrative table showing a hypothetical population's Total Lifetime Attributable Risk, in accordance with an embodiment of the invention;

FIG. 6 shows an illustrative table showing a hypothetical patient's Scaled Lifetime Attributable Risk, in accordance with an embodiment of the invention;

FIG. 7 shows an illustrative table showing a hypothetical patient's Radiation and Diagnostic Study Score with Recent Study Indicator, in accordance with an embodiment of the invention;

FIG. 8 shows an illustrative table showing a hypothetical Previous Study Factor, in accordance with an embodiment of the invention;

FIG. 9 shows an illustrative table showing a hypothetical Time Decay Element, in accordance with an embodiment of the invention;

FIG. 10 shows an illustrative table showing a hypothetical Usage Metric Calculation, in accordance with an embodiment of the invention;

FIG. 15 shows an illustrative table showing a hypothetical record of a patient's radiologic tests, in accordance with an embodiment of the invention;

FIG. 16 shows an illustrative table showing a hypothetical correlation between radiologic tests and a measure of ionizing radiation, in accordance with an embodiment of the invention;

FIG. 17 shows an illustrative graph, not to scale, of General Population Total Lifetime Attributable Risk vs. Scaled Value for Risk, in accordance with an embodiment of the invention;

FIG. 18 shows an illustrative graph, not to scale, of General Population Total Lifetime Attributable Risk vs. Adjusted Scaled Value for Risk, in accordance with an embodiment of the invention;

FIG. 19 shows a portion of a hypothetical patient report, in accordance with an embodiment of the invention;

FIG. 20 shows a portion of a hypothetical patient report, in accordance with an embodiment of the invention;

FIG. 21 shows a portion of a hypothetical patient report, in accordance with an embodiment of the invention;

FIG. 22 shows an illustrative table showing a hypothetical resolution metric calculation, in accordance with an embodiment of the invention;

Figure 11:
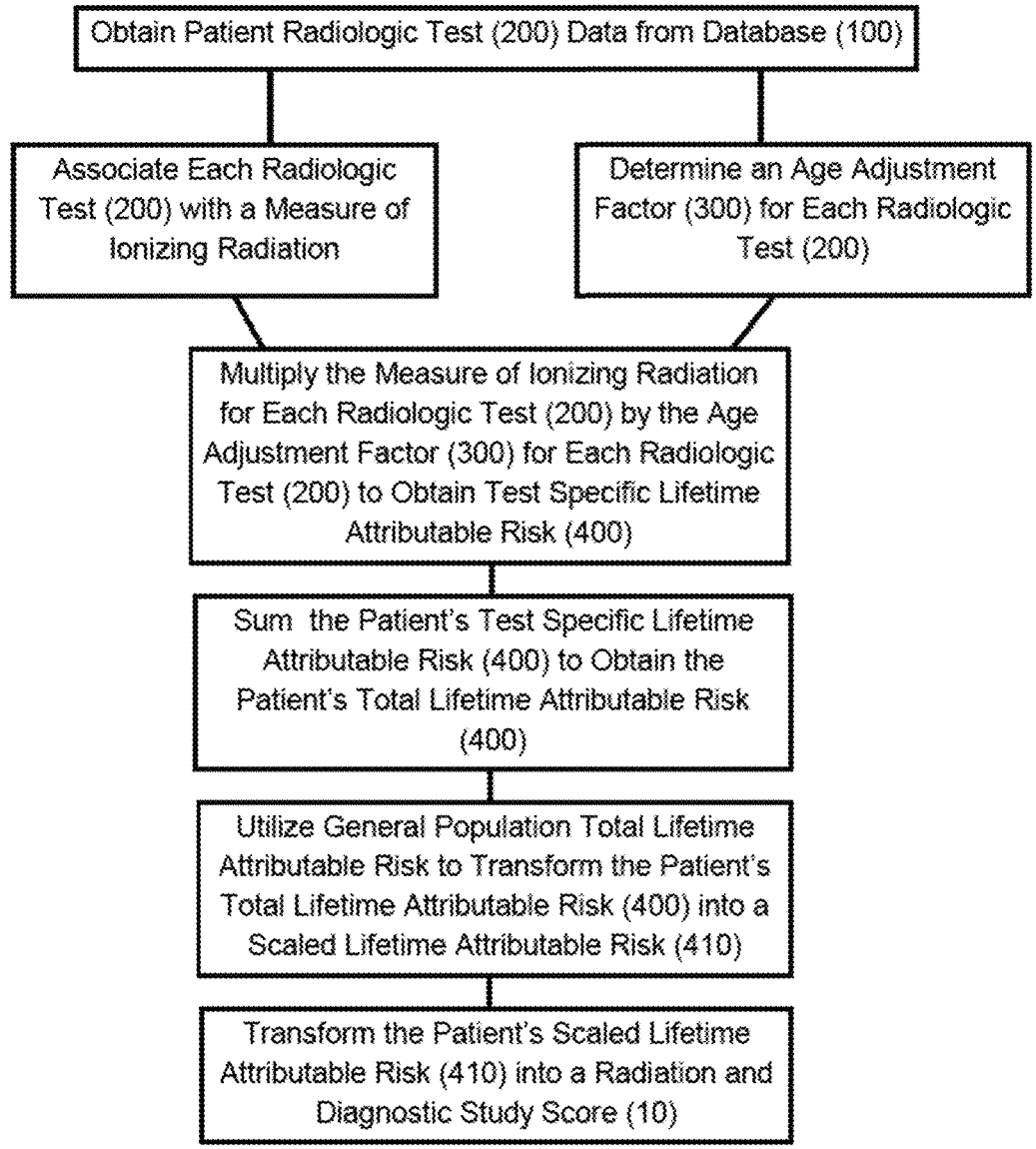
FIG. 11 shows an illustrative diagram of an embodiment of the invention.

These figures are provided to assist in the understanding of exemplary embodiments as described in more detail below and should not be construed as unduly limiting. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The claimed method, system, and computer program product for determining a patient radiation and diagnostic study score (10) and report enables a significant advance in the state of the art.

At the heart of the invention is a radiologic scoring system that raises awareness to the availability of patient specific radiologic information relevant to lifetime attributable risk (400), also referred to as LAR, and diagnostic study usage. This scoring system, which generates values known as radiation and diagnostic study score (10), also referred to as a "rads score", which in some embodiments ranges from 000 to 999. Higher scores translate to greater lifetime attributable risk (LAR). A key element of the scoring system is that even though radiation exposure is theoretically limitless, the radiation and diagnostic study score (10) is range bound. Furthermore, the radiation and diagnostic study score (10) is "naturally relative" as it is based on an assessment of a large study population of individuals who have used diagnostic radiology in the past. The use of a large study population allows for the creation of an intuitive scoring system based on the rank ordered percentile contribution of an individual's risk to the sum total of the population's risk.

To further explain the nature of the radiation and diagnostic study score (10) system, let us evaluate a universe (closed system) of 25 individuals (Persons A-Y), all of variable age, who have been subject to only 5 possible radiologic tests (200) (Test 1-5). Furthermore, let us assume that a history of the radiologic tests (200) performed on each patient has been stored in a database (100) accessible to a score processor.

FIG. 1 represents radiologic test (200) data associated with Patient A found in the database (100) for a scoring period, which in this example is the life of Patient A. This record contains 20 studies all performed at varying times. Each of the patients in the universe has their own record containing similar data. The scoring period is not required to be the life of a patient, but it is preferable when such radiologic test (200) data is available, although such data may not be readily accessible in electronic form for some patients. Generally the scoring period is at least 1 year, preferably at least 5 years, more preferably at least 10 years, even more preferably at least 15 years, and ideally the life of the patient.

Radiology studies that use ionizing radiation increase lifetime attributable risk (400), but not all radiology studies use ionizing radiation. Furthermore, those studies that use ionizing radiation use varying amounts of it. For the purposes of developing a radiation and diagnostic study score (10), the present method assigns a value to each radiologic test (200) in the scoring period that represents the amount of radiation used, if such a measure of ionizing radiation is not readily available in the database (100). The measure of ionizing radiation may be represented in numerous ways and may utilize several choices of units. In one embodiment the measure of ionizing radiation is the Sievert (Sv), which represents the stochastic (or cancer inducing) risk of each study to the whole body. In use, Sieverts are usually represented as milli-Sieverts (mSv) and are dependent on the amount of radiation used and where on the body it is focused. The actual mSv for each radiologic test (200) is dependent on machine settings, imaging protocol, and patient size characteristics. In some cases this actual value can be stored in the database (100). In cases where no mSv is stored, an average value can be assigned based on the type of radiologic test (200). FIG. 2 represents a list of the average mSv values for each of the generic radiologic tests (200), Test 1-5 of this example.

As mentioned above, the cancer inducing risk of ionizing radiation is dependent on the amount and location of the radiation exposure. It is also dependent on the age of the patient as younger patients are both more sensitive to radiation and also have a longer life expectancy over which there is more time for cancer to develop. Studies of the atomic bomb events of World War II have resulted in generally accepted age adjustments for a given amount of radiation exposure. These adjustments have been published, or can be extrapolated from, the Biologic Effects of Ionizing Radiation (BEIR) series of reports. One embodiment of the invention includes an age adjustment factor (300) to scale the measure of ionizing radiation for each radiologic test (200). For the purposes of this example, a sex averaged age adjustment factor (300), also referred to as AAF, is determined by the score processor based on the following formula: age adjustment factor (300)=(2−(age in years/12.5)+1), minimum value=1. This formula effectively yields a value of 3 at age 0 that linearly decreases to 1 at age 25 and then goes no lower. FIG. 3 represents the one exemplary individual age adjustment factor (300) values for ages 1 to 25+. One skilled in the art will appreciate that the score processor may utilize any number of linear or nonlinear declining line or curve methodologies to determine the age adjustment factor (300) starting with an initial value at a young age, preferably birth, and declining to a terminal value at a predetermined age, which is 25 in the present embodiment. The young age is preferably less than 5 years old, more preferably less than 2.5 years, even more preferably less than 1 year, and ideally birth, while the predetermined age of the terminal value is preferably at least 15 years, more preferably at least 20 years, and most preferably at least 25 years. The age adjustment factor (300) is not limited to the example of this one embodiment.

As mentioned above, lifetime attributable risk (400) in the setting of calculating a radiation and diagnostic study score (10) is the extra risk, in this embodiment measured as a percent, of getting cancer from the radiation received during diagnostic imaging occurring during the scoring period. The lifetime attributable risk (400) contribution for each diagnostic study is obtained by the score processor, which calculates the product of the mSv and the lifetime attributable risk (400) for each radiologic test (200) and divides by 100. The patient's total lifetime attributable risk (400) is the sum of the lifetime attributable risk (400) for each radiologic test (200) during the scoring period. FIG. 4 represents the addition of mSv, computed age adjustment factor (300), computed study lifetime attributable risk (400), and computed total lifetime attributable risk (400). In this example, Patient A has acquired an extra 0.77% risk of cancer as a result of their exposure to ionizing radiation during radiologic tests (200).

Knowing that Patient A has acquired an additional 0.77% risk of cancer will help inform a provider as to the current additional risk of cancer for the patient. Certainly, the patient has benefited from at least some of the radiologic tests (200) that were performed in the past so although a provider knows the absolute lifetime attributable risk (400) value, they may have a hard time understanding whether the benefits outweigh the risks. The provider also doesn't know whether the lifetime attributable risk (400) value is below normal, average, or well above normal. If the provider could somehow understand how this patient's lifetime attributable risk (400) measures up to all other patient lifetime attributable risk (400) in the population, they may better understand the context (relative value) and also be able to better predict future risks and benefits.

The database (100) containing Patient A's data may also contain data for other patients in the population, or such general population data may reside in a separate database or quick reference chart, diagram, or equation. Regardless of the form accessed by the score processor, at some point the same methods applied to Patient A are used by a score processor to determine the total lifetime attributable risk (400) for a large quantity of patients that accurately reflect the general population, which in this closed system example of 25 patents includes every patient. Thus, FIG. 5 represents an ordered list of total lifetime attributable risk (400) values for all patients in this exemplary population. Once the total lifetime attributable risk (400) value is known for every patient, the total lifetime attributable risk (400) values can be transformed, via the score processor, to a scaled lifetime attributable risk (410) value representing the rank ordered, percent contribution to the total population lifetime attributable risk (400). This process is demonstrated in FIG. 6. In FIG. 6, one can see that the sum of all patient total lifetime attributable risk (400) values, also thought of as the total population's lifetime attributable risk (400), is 18.6. The "% Contribution" column represents the individual patient's total lifetime attributable risk (400) divided by the total population's lifetime attributable risk (400). The "running total" column represents the sum of the individual patient's total lifetime attributable risk (400), plus all previous lifetime attributable risk (400) values. The scaled lifetime attributable risk (410) column represents a rounded value for the "running total" multiplied by 100. Note that the last running total value "1" is manually changed from 100 to 99 to represent the 99$^{th}$ percentile and to accommodate a phantom patient with a higher score that may one day appear in the population. This process of creating a scaled lifetime attributable risk (410) value utilizes the score processor to transform the raw patient's total lifetime attributable risk (400) values into a scaled value that provides much more insight into the relativity of lifetime attributable risk (400) values. One skilled in the art will appreciate that the general population data need not be analyzed each time a patient's scaled lifetime attributable risk (410) is determined, but may be summarized in a separate database or quick reference chart, diagram, or equation, just to a few embodiments that may simplify the process for large population groups.

In this example Patient L has a total lifetime attributable risk (400) value of 0.45%. The scaled lifetime attributable risk (410) for Patient L is equal to 19. A provider who has a basic understanding of the radiation and diagnostic study score (10) system will understand that a scaled lifetime attributable risk (410) of 19 implies that patients with this level of risk (and lower) comprise about 19% of the total risk in the population. A key threshold in the scaled lifetime attributable risk (410) can be found at a total lifetime attributable risk (400) of 1%. This happens with Patient B. A provider who understands that a scaled lifetime attributable risk (410) value of 50 represents a 1% total lifetime attributable risk (400) will also then understand that any scaled lifetime attributable risk (410) value below 50 represents less than 1% total lifetime attributable risk (400). Furthermore, the additional data point 4.53% total lifetime attributable risk (400)=scaled lifetime attributable risk (410) value of 99 informs a provider on the general shape of the total lifetime attributable risk (400) curve in that it increases one unit in the first half of the scaled lifetime attributable risk (410) value range (0-49) and then quadruples in the last half of the scaled lifetime attributable risk (410) value range (50-99), as seen in FIG. 21. In one embodiment the radiation and diagnostic study score (10) is simply the scaled lifetime attributable risk (410) value, as graphically illustrated in the diagram of FIG. 11.

Figure 12:
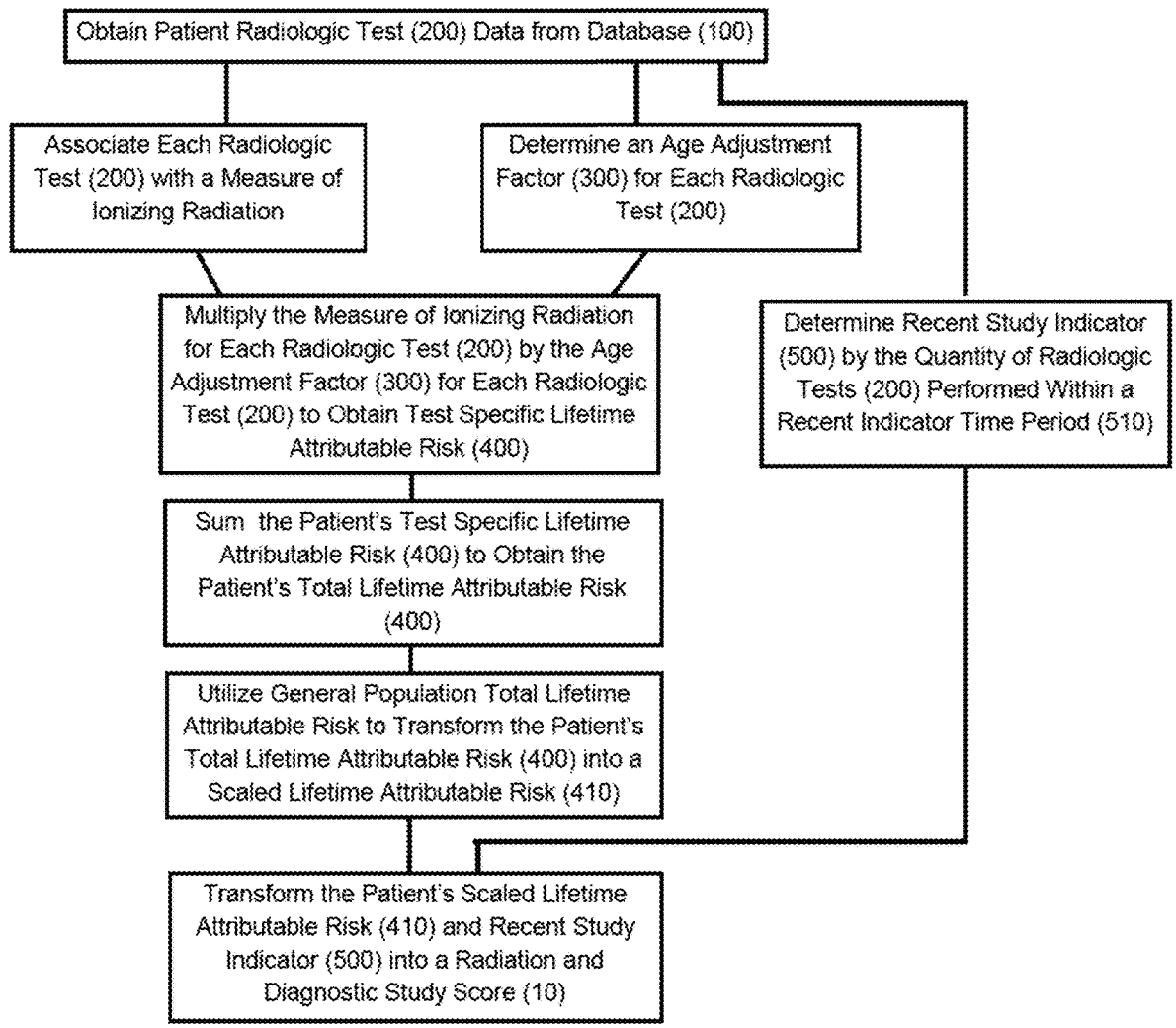
FIG. 12 shows an illustrative diagram of an embodiment of the invention.

In a further embodiment a recent study indicator (500) is incorporated in the process of creating the radiation and diagnostic study score (10). For example in one embodiment the transition from the scaled lifetime attributable risk (410) value to a radiation and diagnostic study score (10) is accomplished by the score processor adding a third digit to the scaled lifetime attributable risk (410) value, wherein the third digit is a recent study indicator (500) which represents the number of recent radiologic tests (200) within a recent indicator time period (510). The recent indicator time period (510) is one year or less, preferably six months or less, or more preferably 90 days or less. The number of radiologic tests (200) within the recent indicator time period (510) can alert a provider to radiology data that may be clinically relevant even when a patient has a low radiation and diagnostic study score (10). FIG. 7 represents the addition of a recent study indicator (500) to the scaled lifetime attributable risk (410) value to create the composite radiation and diagnostic study score (10) of this embodiment. As can be seen in FIG. 7, some patients with a low composite radiation and diagnostic study score (10) have a high recent study indicator (500), or third digit count, indicating several recent radiologic tests (200) within the recent indicator time period (510). For instance, Patient X has a composite radiation and diagnostic study score (10) of 085 and even though a provider knows that patient X has a relatively low scaled lifetime attributable risk (410) (well less than 1%), they also know from looking at the composite radiation and diagnostic study score (10) that Patient X has had 5 radiologic tests (200) within the recent indicator time period (510) so perhaps their clinical interest in Patient X's radiology history should be higher. In this embodiment the composite radiation and diagnostic study score (10) is normalized to 3 digits, by the score processor, with a leading zero when required, and it is also a composite 3 digit number wherein the first two digits represent the scaled lifetime attributable risk (410) value and the third digit represents the recent study indicator (500), or quantity of recent radiologic tests (200) within the recent indicator time period (510), as graphically illustrated in the diagram of FIG. 12.

The radiation and diagnostic study score (10) described above is a unique and innovative approach to quantifying radiation risk and diagnostic study usage and packaging it in a manner that is easy to store, transport, and recognize. The radiation and diagnostic study score (10) can be used as a visual trigger raising the general awareness of a treating provider but it can also be used as a discrete data element used within a computerized clinical decision support application. For example, if a provider was going through the process to electronically order a CT Scan for a patient, an alert could be provided in real-time if the patient has a radiation and diagnostic study score (10) above a predetermined score alert value (600), or if the recent study indicator (500) is above a predetermined recent study alert value (520), or if the same radiologic test (200) has been performed within a prior study period.

In another embodiment, the radiation and diagnostic study score (10) and other relevant information is transformed by the score processor into a report (700) format that may further explain the types of radiological tests (200) contributing to the score and when they were performed. Relative scoring information may also be included in the report (700) to help contextualize the numerical values and to aid patient education, should it be deemed necessary. An example of a report (700) is seen in FIGS. 19-21, which will be described later in more detail.

A living patient's record is not static and one can anticipate that a patient's radiology record will change, perhaps quite frequently. To be most effective and useful, a radiation and diagnostic study score (10) (and report) may be computed in real-time at the point and time of service. This requires frequent updates of aggregated data, or the use of a real-time query system for distributed data.

While the above recent study indicator (500) embodiment having the last digit of the radiation and diagnostic study score (10) represents one measure of usage, a more sophisticated measurement of usage can be made using a similar method as the lifetime attributable risk (400) and scaled lifetime attributable risk (410), using the calculations and transformations previously described. Whereas the lifetime attributable risk (400) measurement is the product of the measure of ionizing radiation, mSv in this example, and the age adjustment factor (300), another usage metric embodiment utilizes the product of two other variables, namely a previous study factor (800), also referred to as a PSF, and a time decay element (900), also referred to as a TDE.

The previous study factor (800) represents the number of times an individual radiologic test (200) has been repeated for a patient. The belief in tracking this particular metric is that the more times an individual radiologic test (200) is repeated the less the probable utility of each additional radiologic test (200) of the same type. A number of equations can be designed to generate the previous study factor (800). In one embodiment the previous study factor (800) may be represented by the equation:

$$\text{previous study factor}(800) = \ln(\text{repetitive test number}(810)) + 1$$

where a repetitive test number (810) represents the number of times the radiological test (200) has been performed. For this particular embodiment, FIG. 8 represents the previous study factor (800) value for the first 20 times, repetitive test numbers (810) 1-20, a radiologic test (200) is ordered using the formula of this embodiment. In this embodiment the previous study factor (800) increases in a non-linear manner as a result of the example logarithmic function. Alternatively, in another embodiment the previous study factor (800) is a fixed value generated by simply counting whether or not a study represents a repeat; thus in a further embodiment the previous study factor (800) is a 0 or a 1. One skilled in the art will appreciate that the score processor may utilize any number of growth modeling techniques.

The time decay element (900) represents the amount of time that has passed since a radiologic test (200) has been performed. The belief in tracking this particular metric is that the more time that has elapsed since a radiologic test (200) was performed, the less important that individual radiologic test (200) data is when considering whether to order additional radiologic tests (200). A number of equations can be designed to generate the time decay element (900). In one embodiment the time decay element (900) may be represented by the equation:

$$\text{time decay element}(900) = 0.999^{(\text{number of days elapsed})}$$

For this particular embodiment, FIG. 9 represents the time decay element (900) value for 10 days increments of elapsed time using this formula. One skilled in the art will appreciate that the score processor may utilize any number of declining curve methodologies, including, but not limited to, exponential, hyperbolic, and harmonic.

A usage metric (1000), which is the product of the previous study factor (800) and the time decay element (900), using the above example formulas, is depicted for Patient A in FIG. 10. One skilled in the art will appreciate that this usage metric (1000) can be transformed by the score processor into a scaled usage metric (1010) by considering a representative sample of the general population in the same manner as previously explained with respect to the total lifetime attributable risk (400) being transformed into a scaled lifetime attributable risk (410), thereby resulting in a scaled usage metric (1010) ranging from 0-99 as graphically illustrated in the diagram of FIG. 13.

This scaled usage metric (1010) can be used by the score processor to sort out patients along the lines of recent and repetitive testing. It can also be combined with the scaled lifetime attributable risk (410) in a weighted fashion to generate a composite score representing risk and usage. For instance in one embodiment if Patient A were determined to have a scaled lifetime attributable risk (410) of 36 (as demonstrated in the examples above) and a scaled usage metric (1010) of 54, an equally weighted composite radiation and diagnostic study score (10) would be equal to 36/2+54/2=45. Further, in an additional embodiment incorporating a third digit representing the recent study indicator (500), or quantity of recent radiologic tests (200) within the recent indicator time period (510), if Patient A had 2 recent radiologic tests (200) within the recent indicator time period (510), a further composite radiation and diagnostic study score (10) would be equal to 452, as graphically illustrated in the diagram of FIG. 14.

In the previous embodiment the weighting of the scaled lifetime attributable risk (410) and the scaled usage metric (1010) was equal, thus a scaled LAR weighting factor (420) was 0.5 and a scaled usage weighting factor (1020) was 0.5. One skilled in the art will realize that the scaled LAR weighting factor (420) and the scaled usage weighting factor (1020) could be as low as zero, provided their sum adds up to 1.0. Thus, in the prior example explained with reference to FIGS. 1-7, the composite radiation and diagnostic study score (10) can be thought of as being determined using a scaled usage weighting factor (1020) of zero and represents a pure scaled lifetime attributable risk (410) score. Conversely, a composite radiation and diagnostic study score (10) with a scaled LAR weighting factor (420) of zero would represent a pure scaled usage metric (1010) score. Independent of any composite scoring methodology the scaled lifetime attributable risk (410) and the scaled usage metric (1010) represented in this document represent two individually useful metrics that may be used independent of one another to sort and report on large populations of patients. In one further embodiment the scaled LAR weighting factor (420) ranges from 0.2 to 0.8, the scaled usage weighting factor (1020) ranges from 0.2 to 0.8, and the sum of the scaled LAR weighting factor (420) and the scaled usage weighting factor (1020) is 1.0, while in an even further embodiment the scaled LAR weighting factor (420) ranges from 0.4 to 0.6, the scaled usage weighting factor (1020) ranges from 0.4 to 0.6, and the sum of the scaled LAR weighting factor (420) and the scaled usage weighting factor (1020) is 1.0.

Yet another usage metric can be made using a similar method as the lifetime attributable risk (400) and scaled lifetime attributable risk (410), as well as the usage metric (1000) and the scaled usage metric (1010), using the calculations and transformations previously described. For instance, the general process of (1) assigning a variable to a radiologic study, (2) summing the values of that variable for individual patients, and (3) creating a scaled metric by comparing the individual's sum to a plurality of the population can be used with any metric of value.

For example, the radiation and diagnostic scores (10) described above are heavily weighted towards radiological tests (200) that use ionizing radiation. However, many types of radiologic tests (200) involve no radiation whatsoever (i.e. MRI) but yield some of the highest quality images obtainable. Thus, knowledge of previous high-resolution images may eliminate the need for further testing of the same region using lower resolution approaches such as plain film x-ray. For this reason, in yet another embodiment a variable that captures the resolution value of previous studies will add to the utility of the radiation and diagnostic scores (10).

A resolution metric (1100) can be derived by assigning a resolution value approximately equivalent to the amount of ionizing radiation used in a radiologic test (200), with the general understanding that more radiation generally results in high resolution or more complex images. A different approach to assigning a resolution metric (1100) for radiologic tests (200) that don't use ionizing radiation (i.e. MRI and ultrasound) is required. In the case of these two modalities, a MRI can be thought of as being generally equivalent to a CT Scan, and an ultrasound can be generally thought of as equivalent to plain film x-rays. As such, in one embodiment a MRI can be assigned a resolution metric (1100) equal to the average of all CT Scans and an ultrasound can be assigned a resolution metric (1100) equal to the average of all plain film x-rays.

Alternatively, in a further embodiment another method of resolution assignment for individual radiologic tests (200) may utilize a third party system that generally captures the radiologic complexity of the study involved. For example, Relative Value Units (RVUs) as dictated by Medicare are assigned to every CPT code and generally represent the expertise required, associated practice expense, and liability expense. In practice, a radiologic reading of an MRI of an extremity may have an RVU assignment of approximately 2 and a plain film x-ray of the same region may have an RVU assignment of approximately 0.2.

FIG. 22 represents a total resolution metric (1100) calculation for Patient A. In this example, the radiation dose values, in mSv, from FIG. 2 are used to as the resolution metric (1100) for radiologic tests (200) associated with ionizing radiation. However, as seen in FIG. 2, test 5 did not have an associated radiation dose value, thus a value of zero was used in FIG. 4. Now, we are going to account for this radiologic test (200) by assigning it a resolution metric (1100) equal to the highest mSv value, namely a resolution metric (1100) of 20 as seen in FIG. 22. This example calculation is consistent with Test 4 being representative of a CT Scan and Test 5 representing an MRI. Thus, in this embodiment the use of a resolution metric (1100) accounts for radiologic tests (200) associated with ionizing radiation, as well as those that are not associated with ionizing radiation but should be factored in to the creation of the radiation and diagnostic study score (10).

A total resolution metric (1100) is depicted for Patient A in FIG. 22. One skilled in the art will appreciate that this resolution metric (1100) can be transformed by the score processor into a scaled resolution metric (1110) by considering a representative sample of the general population in the same manner as previously explained with respect to (a) the total lifetime attributable risk (400) being transformed into a scaled lifetime attributable risk (410), and (b) the patient's total usage metric (1000) into a scaled usage metric (1010), thereby resulting in a scaled resolution metric (1110) ranging from 0-99 as graphically illustrated in the diagram of FIG. 23. Alternatively, the total resolution metric (1100) calculation for Patient A shown in FIG. 22, may assign a resolution metric (1100) of zero for radiologic tests (200) associated with ionizing radiation because some embodiments incorporating a scaled lifetime attributable risk (410) have already accounted for these radiologic tests (200), and then, in this case, the total resolution metric (1100) and the scaled resolution metric (1110) represent the additional consideration associated with radiologic tests (200) that are not associated with ionizing radiation.

Figure 23:
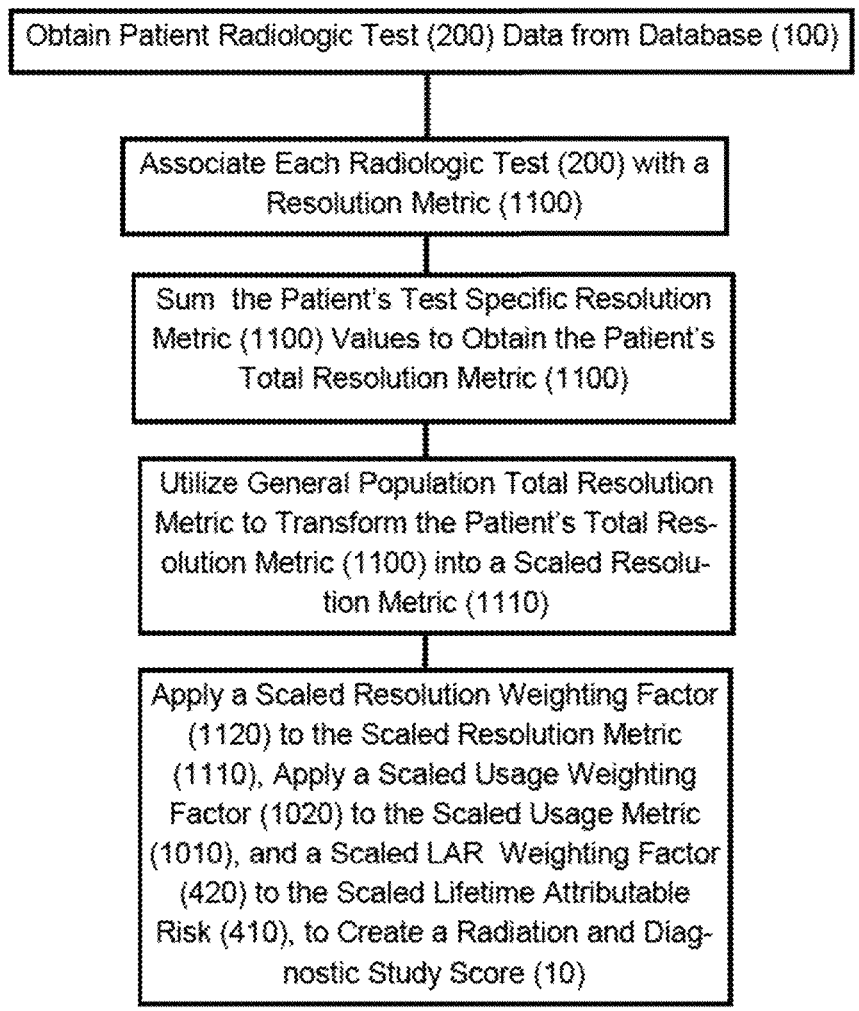
FIG. 23 shows an illustrative diagram of an embodiment of the invention.
Figure 24:
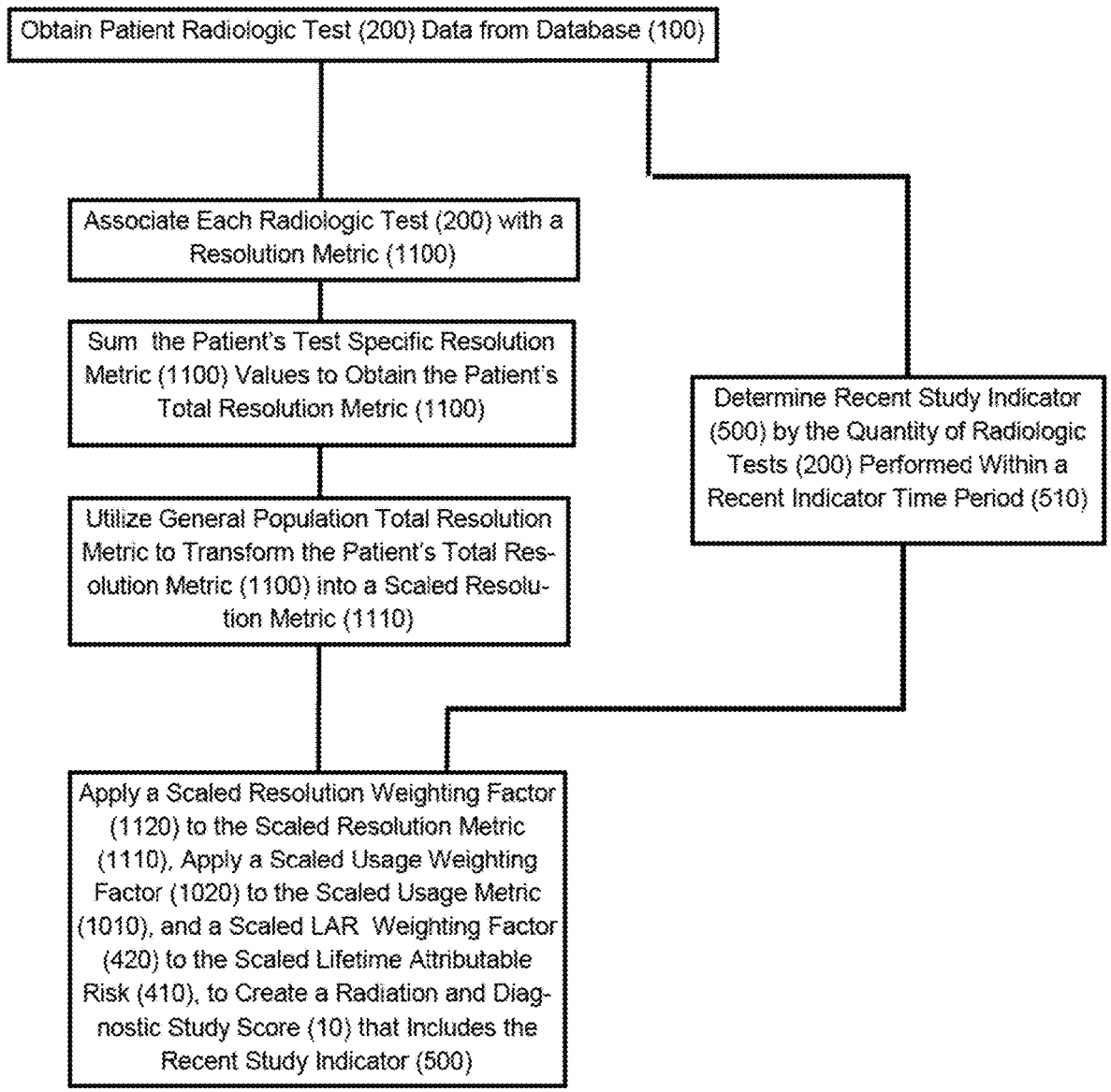
FIG. 24 shows an illustrative diagram of an embodiment of the invention.

Regardless of the actual method used to assign a resolution metric (1100) value to the radiologic tests (200), as seen in FIGS. 23 and 24, one skilled in the art will appreciate that a scaled resolution metric (1110) can be generated and used in the same manner as the scaled usage metric (1010) described above. This scaled resolution metric (1110) can then be incorporated into the radiation and diagnostic scores (10) through the application of a scaled resolution weighting factor (1120).

This scaled resolution metric (1110) can also be combined with the scaled lifetime attributable risk (410) and/or the scaled usage metric (1010) in a weighted fashion to generate a composite score. For instance in one embodiment if Patient A were determined to have a scaled lifetime attributable risk (410) of 36 (as demonstrated in the examples above), a scaled usage metric (1010) of 54, and a scaled resolution metric (1110) of 24, an equally weighted composite radiation and diagnostic study score (10) would be equal to 36/3+54/3+24/3=38. The weighted composite radiation and diagnostic study score (10) may include any combination of weighting 2 or more of the scaled resolution metric (1110), the scaled lifetime attributable risk (410), and/or the scaled usage metric (1010). Further, in an additional embodiment incorporating a third digit representing the recent study indicator (500), or quantity of recent radiologic tests (200) within the recent indicator time period (510), if Patient A had 2 recent radiologic tests (200) within the recent indicator time period (510), a further composite radiation and diagnostic study score (10) would be equal to 382, as graphically illustrated in the diagram of FIG. 24.

Figure 13:
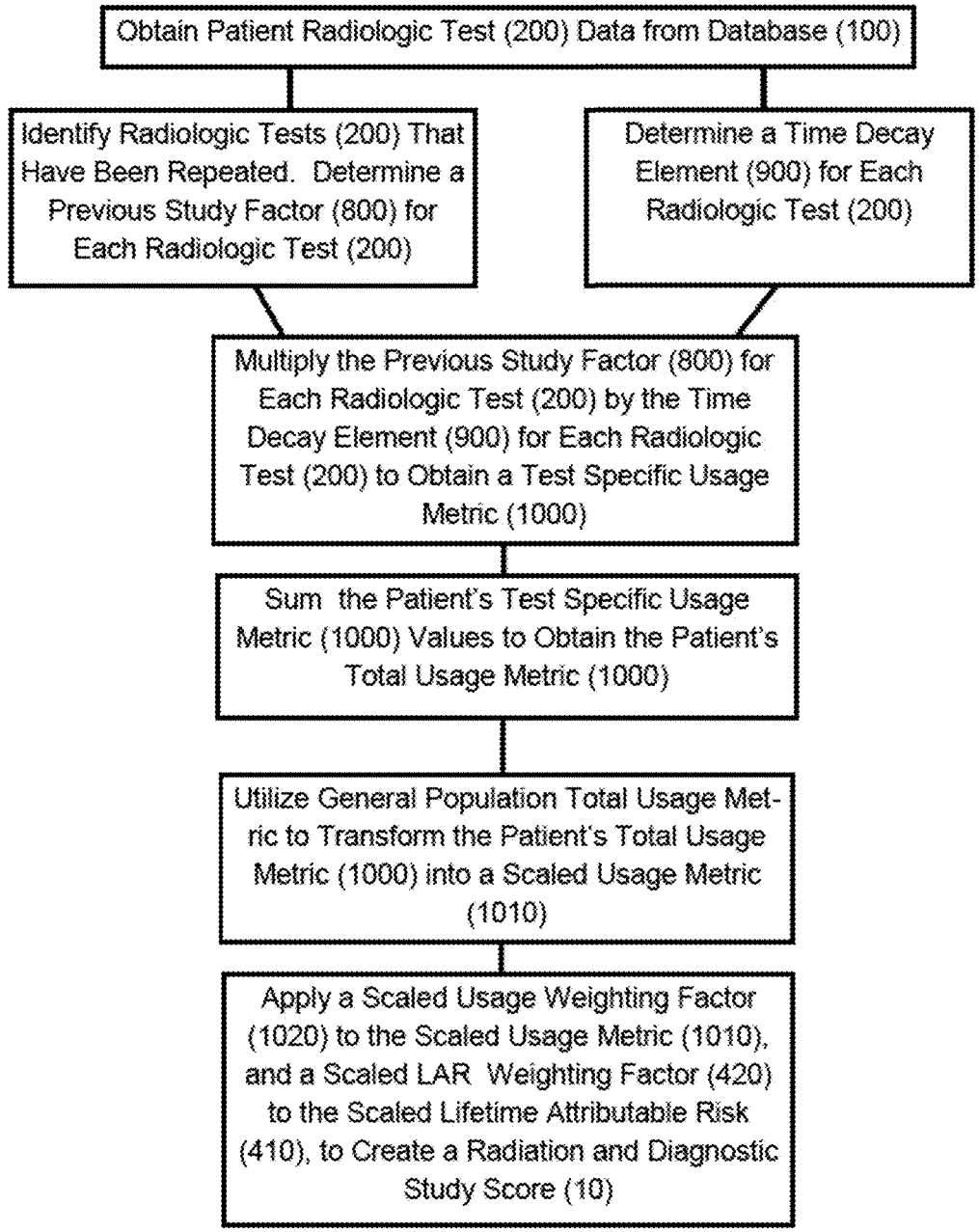
FIG. 13 shows an illustrative diagram of an embodiment of the invention.
Figure 14:
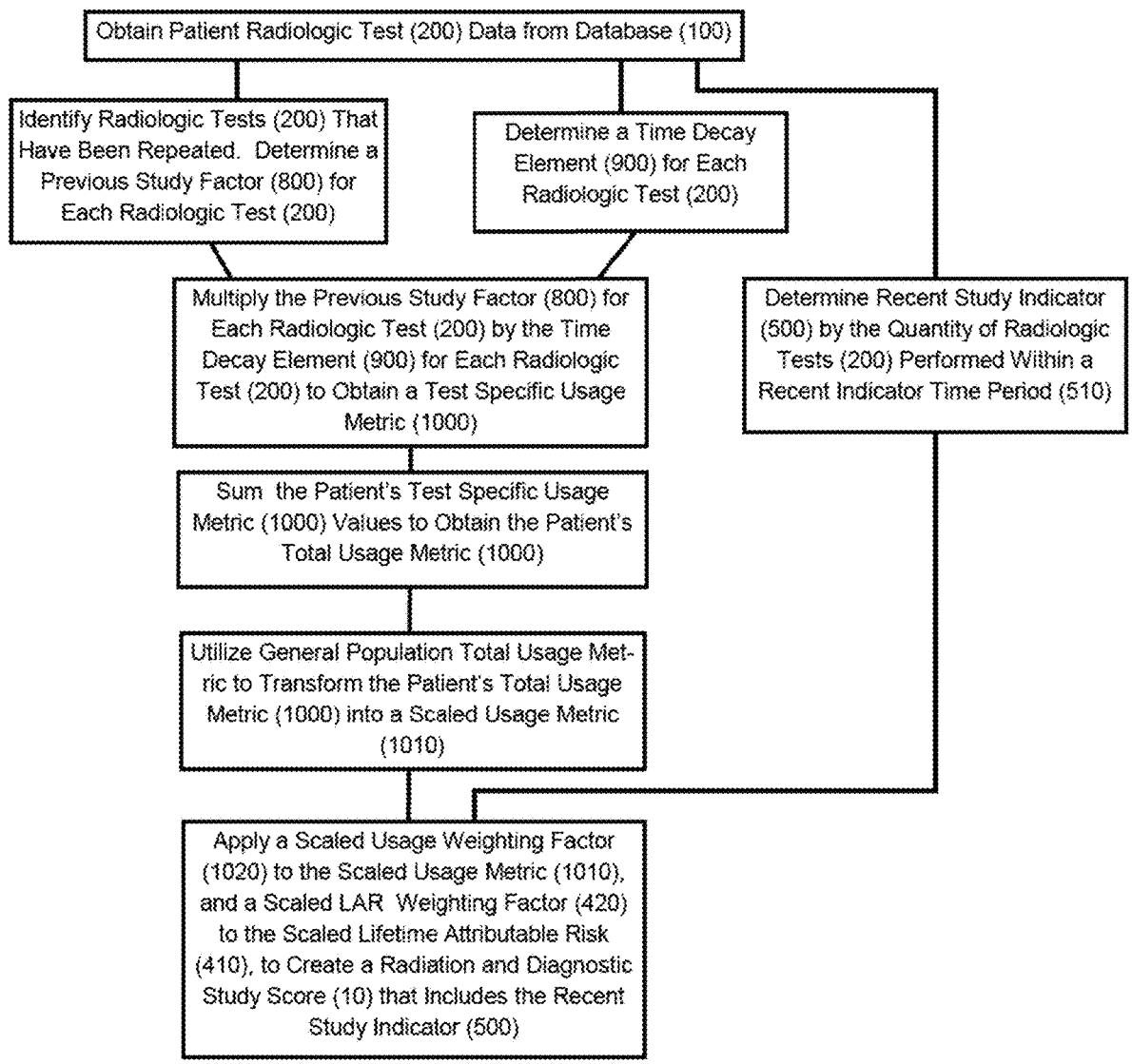
FIG. 14 shows an illustrative diagram of an embodiment of the invention.

In the previous embodiment the weighting of the scaled lifetime attributable risk (410), the scaled usage metric (1010), and the scaled resolution metric (1110) were equal, thus a scaled LAR weighting factor (420) was ⅓, a scaled usage weighting factor (1020) was ⅓, and a scaled resolution weighting factor (1120) was ⅓. One skilled in the art will realize that the scaled LAR weighting factor (420), the scaled usage weighting factor (1020), and the scaled resolution weighting factor (1120) can be as low as zero, provided their sum adds up to 1.0. Independent of any composite scoring methodology the scaled lifetime attributable risk (410), the scaled usage metric (1010), and the scaled resolution metric (1110) represented in this document represent individually useful metrics that may be used independent of one another. For instance, having a scaled LAR weighting factor (420) of 1.0, with a scaled usage weighting factor (1020) of zero, and a scaled resolution weighting factor (1120) of zero, effectively results in the radiation and diagnostic score (10) methodologies illustrated in FIGS. 11 and 12. Yet some health care providers may want to utilize a radiation and diagnostic score (10) methodology that is more influenced by repeated radiologic tests (200), in which case a scaled usage metric (1010) is factored in by having a non-zero scaled usage weighting factor (1020), as illustrated in FIGS. 13 and 14. Even further, some health care providers may want to utilize a radiation and diagnostic score (10) methodology that does not ignore radiologic tests (200) that are not associated with ionizing radiation. In this situation the health care provider may want to utilize a radiation and diagnostic score (10) methodology incorporating the resolution metric (1100) procedure alone, or weight it in combination with lifetime attributable risk (410) and/or the scaled usage metric (1010), as illustrated in FIGS. 23 and 24. Thus, the many embodiments disclosed provide a health care provider to consider many different factors in arriving at a radiation and diagnostic score (10). Therefore it is anticipated that one health care system may prefer a radiation and diagnostic score (10) that only considers radiologic tests (200) associated with ionizing radiation; while a second health care system may a prefer radiation and diagnostic score (10) that is influenced by repeated radiologic tests (200), as would be the case with a methodology incorporating the usage metric (1000); while a third health care system may prefer a radiation and diagnostic score (10) that is influenced by radiologic tests (200) that are not associated with ionizing radiation.

In one embodiment the scaled LAR weighting factor (420) ranges from 0.1 to 0.8, the scaled usage weighting factor (1020) ranges from 0.1 to 0.8, the scaled resolution weighting factor (1120) ranges from 0.1 to 0.8, and the sum of the three weighting factors is 1.0; while in another embodiment the scaled LAR weighting factor (420) ranges from 0.2 to 0.6, the scaled usage weighting factor (1020) ranges from 0.2 to 0.6, and the scaled resolution weighting factor (1120) ranges from 0.2 to 0.6, and the sum of the three scaled weighting factors is 1.0; and in an even further embodiment the scaled LAR weighting factor (420) ranges from 0.5 to 0.9, while the scaled usage weighting factor (1020) and the scaled resolution weighting factor (1120) are each less than 0.5.

The above examples utilize a closed universe of 25 individuals (Persons A-Y), all of variable age, who have been subject to only 5 possible radiologic tests (Test 1-5) in an effort to simplify the explanation of a complex invention, however one skilled in the art will appreciate that this invention is preferably applied to an open system in which people are added to, and removed from, the database (100) regularly. Similarly the example was limited to 5 possible radiologic tests (200), a fraction of those present in the real world. Additional examples of radiologic test (200) data are seen in FIG. 16.

The previously mentioned database (100) may reside on a state medical system server, however one skilled in the art will appreciate that the database (100) described herein is not limited to a statewide system or a federal system, as it may be a hospital specific database, a commercial database, a data aggregator database, an insurance company database, or community specific database (100). Similarly, the database (100) need not reside on a server but rather may reside on a local memory device in a standalone manner, and further, in anticipation of advances in health care IT infrastructure, the database (100) may be created for an individual patient by broadly electronically querying a network of health care providers and aggregating the collected data, which may be completed in virtually real-time. The radiologic test (200) data may be found in numerous locations. A hospital or imaging center may store the information within its own Radiology Information System (RIS). A Health Information Exchange (HIE) may hold references to the RIS data, or the actual RIS data, for many regionally related hospitals. Billing information containing radiology data is transmitted to insurers for payment and creates yet another source of radiology data, namely a database of Current Procedural Terminology (CPT) codes, Revenue Codes, and Health Care Common Procedure Coding System (HCPCS) Codes, aggregated at the insurer level. Because patients often obtain diagnostic radiology services at a variety of locations, data aggregators such as an HIE or insurance company represent some of the best sources of data, however one skilled in the art will appreciate that the database (100) described herein is not limited to any of the above. Similarly, the database (100) need not reside on a server but rather may reside on a local memory device in a standalone manner, and further, in anticipation of advances in health care IT infrastructure, the database (100) may be created for an individual patient by broadly electronically querying a network of health care providers and aggregating the collected data, which may be completed in virtually real-time. Regardless of the scope, location, or creation of the database (100), it contains at least one of record indicative of the imaging studies performed on a patient.

One illustration of patient data available in a database (100) is seen in FIG. 15. A record may contain patient data and radiologic test (200) data. Patient data may include information such as a unique patient ID and/or a patient birth date, in addition to any number of additional patient specific data that is not relevant to the present discussion. Radiologic test (200) data may include information such as imaging billing code(s), imaging identifiers indicative of the type of imaging study performed and the area of the patient exposed to the study, the imaging date, and the imaging provider. In many cases, the record for a patient contains duplicate references to the same imaging event. This may occur as a result of a hospital submitting a bill capturing the technical performance of a CT Scan and a provider submitting a separate bill for the professional reading of the CT Scan. Addendums to previously completed studies are another possible source of duplicity. Additionally, differences can exist in the date of service for the same study (where it is performed on one day and read on the next) and how individual studies are classified. The end result of the duplicates and differences is that a collection of radiology records for a single patient often must be reduced to the set of studies that correspond to the set of singular imaging events at the source of all records. One skilled in the art will appreciate that many methods of alternative design may be required to properly combine, normalize, and de-duplicate data from disparate sources. In one particular embodiment the imaging data consists solely of one or more billing codes and imaging dates, then the radiological exposure processor must then correlate the billing codes to radiologic tests (200), which may include the use of a billing code correlation protocol and/or database. For example, it is not uncommon for a single radiologic test (200) to result in three or four billing codes in the database (100). Thus, the billing code correlation protocol and/or database recognizes common billing code combinations for certain radiologic tests (200) and transforms the billing-code specific data into a record that is radiologic test (200) or procedure specific. For instance to arrive at a radiologic test (200) of a "CT Head" the radiological exposure processor may need to recognize multiple imaging billing codes commonly associated with a CT imaging study, and perhaps additional imaging billing codes to ascertain that the CT imaging study was associated with a specific area of the body, such as the head in this example. Thus, the type of radiologic test (200) may be readily available in the database (100) or it may need to be established by the billing code correlation protocol and/or database.

As previously mentioned, the act of creating the scaled lifetime attributable risk (410), and in some embodiments the scaled usage metric (1010) and/or a scaled resolution metric (1110), consists of comparing a particular patient's total lifetime attributable risk (400), within the study period, with the total lifetime attributable risk associated with a large pool of patients that accurately represent the general population. In one embodiment the large pool of patients contains at least 1000 patients, while another embodiment contains at least 500,000 patients, and in an even further embodiment contains at least 1,000,000 patients. In the big picture the comparison simply results in at least an indication of where the patient data ranks when compared to similar data that is representative of a larger population of patients. For example, one embodiment may simply identify whether the patient data is in a below normal range, a normal range, or an above normal range when compared to a larger population of patients. Alternatively, another embodiment may determine a percentile ranking of the patient data compared to the larger population of patients.

As previously discussed, a scaled lifetime attributable risk (410) is derived by comparing the patient's total lifetime attributable risk (400) with the total lifetime attributable risk (400) for a plurality of the general population. In one embodiment this comparison is scaled to a value that is proportional to the percentile ranking of the individual patient risk within the general population. As such, the scaled lifetime attributable risk (410) value for all patients will fall within a range of 0 to 99. The method of determining the scaled values is based on calculating the total lifetime attributable risk (400) for a large group of patents that accurately reflect the general population and rank ordering them from lowest to highest. The % contribution to total population lifetime attributable risk is assigned to each patient and the patient's individual contributions are then added until an integer percentage is obtained. The total lifetime attributable risk values at each integer transition point are used to establish a range for which all total lifetime attributable risk values equate to a single scaled lifetime attributable risk (410) between 0-99. Calculating the total lifetime attributable risk for the large group of patients and determining integer transition points results in the graph seen in FIG. 17.

In order to impart even more meaning into the radiation and diagnostic study score (10), in one embodiment the reference tables that form the foundation of the comparative scoring paradigm were uniformly transformed to align with recognizable risk data points inherent in medicine. One simple, key risk metric in medicine is 1%. This metric aids many conversations and thoughts about risk as it represents a 1 in 100 chance. For example, when discussing subarachnoid hemorrhage as a source of headache, the incidence in the emergency department population of patients presenting with headache is thought to be approximately 1%. This 1% risk of subarachnoid hemorrhage has led to a strong emphasis on detection, and has resulted in very sophisticated and detailed workup strategies. Thus, in one embodiment, when creating a patient's scaled lifetime attributable risk (410), the population curve was shifted (intact) such that a scaled lifetime attributable risk (410) value of 50 equates to 1% lifetime attributable risk (400). This shifted population curve, seen in FIG. 18 results in a scaled lifetime attributable risk (410) value of 99 being equal to 10% or greater LAR.

Regardless of exact embodiment previously disclosed, knowing that a patient has a radiation and diagnostic study score (10) of 805 informs the provider of several key historical facts. On a scale of 000 to 999, an 805 is obviously skewed to the higher range and represents a relatively high radiation exposure level. In light of the unique way the population incidence of risk was used to generate the scaled scores, the provider knows that a person with a radiation and diagnostic study score (10) of 805 has a much higher (and rarer) exposure history than a patient with a radiation and diagnostic study score (10) of 305. With knowledge and understanding of the relationship between total lifetime attributable risk (400) and the radiation and diagnostic study score (10) system, the provider can also deduce that the patient with a radiation and diagnostic study score (10) of 805 has a lifetime attributable risk of approximately 3%. Further, clearly this example is an embodiment having a recent study indicator (500), thus the 5 in the radiation and diagnostic study score (10) of 805 indicates there are several recent radiologic tests (200) the provider should be aware of.

As a result of the methodology used in creating the radiation and diagnostic study score (10) system, providers will now have access to an intuitive scoring system that matches with their clinical expectation and matches with the prevalence of radiology usage and radiation exposure within the general population. Providers will be able to easily compare patient scores and associated risk and more easily explain to patients what their risk score means in real terms. In some embodiments a provider will be able to explain to a patient that a score of 500 means they have acquired an approximate 1% additional risk of cancer, and if their score continues to increase, they will approach a 10% or greater additional risk as they get closer to a radiation and diagnostic study score (10) of 990, as seen in FIG. 21. Thus, one embodiment further includes the step of scaling the general population radiologic test data so that the total lifetime attributable risk (400) of approximately unity is associated with a predetermined scaled lifetime attributable risk (410). In an even further embodiment the predetermined scaled lifetime attributable risk (410) associated with the total lifetime attributable risk (400) of approximately unity is approximately 50. Similarly for the total usage metric, one embodiment further includes the step of scaling the general population radiologic test data so that the total usage metric (1000) of approximately unity is associated with a predetermined scaled usage metric (1010). In an even further embodiment the predetermined scaled usage metric (1010) associated with the total usage metric (1000) of approximately unity is approximately 50.

Initial studies on a large population of almost 900,000 patients reveal that approximately 1-2% of the population has a radiation and diagnostic study score (10) of 500 or greater. This 1-2% of the population also accounts for about 25% of the CT Scans and associated radiation exposure in the entire population, so although one would expect that a score of 500 would be rarely seen, this initial study predicts that about 1 in 4 CT scans will be performed on a patient with a score of 500 or greater.

Throughout this document there are multiple references to a step of comparing a quantity with the plurality of general population data to determine a scaled value, whether it be the scaled lifetime attributable risk (410), the scaled usage metric (1010), or the scaled resolution metric (1110). In some of the many disclosed embodiments the determination of an alert value includes a determination of whether the quantity is within an acceptable range or an unacceptable range, however other embodiments determine approximate percentile rankings of the quantity compared to the general population data. In one embodiment the general population radiological exposure data referenced is data associated with at least 1000 patients over the period of interest. In one embodiment this general population data is present in the database (100) and is extracted by the score processor for use in arriving at the scaled values. The general population data need not be extracted by the score processor each time patient specific data is retrieved from the database (100); rather the general population data may be extracted after extended intervals, which may be months or even years. Therefore, the act of comparing a quantity with the plurality of general population data to determine a scaled value may include the step of previously acquiring the general population data, processing the data, converting the data into a quickly accessible electronic format, and storing the converted data on hardware for use in determining the radiation and diagnostic study score (10) in less than 5 seconds, whether the general population is local or on a hardware device on the other side of the planet. Thus, in one embodiment a local score processor securely retrieves and stores into memory patient specific data from a database (100), the local score processor securely retrieves and stores into memory previously compiled and transformed data representative of the general population radiological exposure, the local score processor retrieves portions of this stored data to form and store at least a scaled lifetime attributable risk (410) value, and transform the data into the radiation and diagnostic study score (10), and the local score processor formats and transmits the radiation and diagnostic study score (10) to display on a visual media. Further, in light of confidential patient data security, the local score processor may then clear the patient specific data from the local memory, as well as leave a timestamp within the remote database (100) to serve as an indicator of when a patient's data was accessed. The score processor may further securely transmit the radiation and diagnostic study score (10) back to the database (100) for storage and retrieval during subsequent data requests. Thus, a system for carrying out the determination of a radiation and diagnostic study score (10) may consist of several securely connected pieces of hardware communicating with the specially programmed score processor to determine the radiation and diagnostic study score (10). As the local score processor retrieves the patient specific data from the database (100), it may create a local patient-specific database for temporarily storing and processing data. The local patient-specific database may be cleared of patient specific data upon the creation of the radiation and diagnostic study score (10) and any associated reports that are simultaneously created.

The score processor is a specially programmed computer device such as a personal computer, a portable phone, a multimedia reproduction terminal, a tablet, a PDA (Personal Digital Assistant), or a dedicated portable terminal that can perform the secure retrieval and processing of input, output, storage and the like of information. It goes without saying that such a program can be distributed through a recording medium such as a CD-ROM and a transmission medium such as the Internet. Further, the present invention may be a computer-readable recording medium such as a flexible disk, a hard disk, a CD-ROM, an MO, a DVD, a DVD-ROM, a DVD-RAM, a BD (Blu-ray Disc), flash drives, thumb drives, and a semiconductor memory that records the computer program. Thus, the distributed program may be used to program a computer to create a score processor thereby becoming a special purpose computer to securely perform particular functions pursuant to instructions from program software.

The radiation and diagnostic study score (10) and/or report (700) may be displayed on visual media. Such visual media referenced herein may be a Cathode Ray Tube (CRT) monitor, a Liquid Crystal Display (LCD) monitor, a plasma monitor, a PC, a laptop, a tablet, a smart phone, a projector and screen, paper, and/or any other such visual display device known to those of ordinary skill in the art.

The development of a mechanism to generate an intuitive and meaningfully rich radiation and diagnostic study score (10) significantly advances the state of art. It may be preferable to also have a radiation and diagnostic study score (10) distribution and report mechanism to reach maximum effect. The report (700) is the vehicle for communicating the details behind the radiation and diagnostic study score (10). The report also guides the provider in understanding the radiation basics behind the assessment and enables individually relevant discussions with the patient. FIG. 19 illustrates one embodiment of a front page of the report (700), and FIGS. 20 and 21 illustrates one embodiment of a rear page of the report (700), which demonstrates how the steps required to generate the score can be broken down and displayed in a clinically meaningful manner.

One particular embodiment of FIG. 19 shows a report (700) in which the score processor has transformed the raw data into a graphic "study timeline" section in which the frequency and relative amount of ionizing radiation associated with a patient's radiologic tests (200) can be easily visualized. Each vertical bar represents a radiologic test (200) and the height of the vertical bar is an indication of the amount of ionizing radiation associated with the particular radiologic test. In a further embodiment, imaging studies not associated with ionizing radiation such as MRI's and ultrasounds are also displayed in the graphical "study timeline," but are separate from the ionizing radiation radiologic tests (200), in this case below the x-axis timeline, to further aid a provider in identifying duplicative imaging studies; however, as previously disclosed such non-ionizing radiation radiologic tests (200) may be incorporated in the radiation and diagnostic study score (10) via associating them with a resolution metric (1100).

The distribution mechanism for the radiation and diagnostic study score (10) and report (700) can be as hard copy, an electronic image file such as a PDF, a web service that accepts patient IDs and returns a radiation and diagnostic study score (10) as data and reports (700) as an image file, and additionally can adhere to an HL7 message standard and provide the scores and report as results. The report (700) can also be delivered as an interactive web page that allows the user to drill down and obtain finer detail to include impression and finding data. One skilled in the art will recognize that a multitude of distribution mechanisms exist for the scores and reports, and the above represent only an exemplary subset of the embodiments.

Numerous alterations, modifications, and variations of the preferred embodiments disclosed herein will be apparent to those skilled in the art and they are all anticipated and contemplated to be within the spirit and scope of this application. For example, although specific embodiments have been described in detail, those with skill in the art will understand that the preceding embodiments and variations can be modified to incorporate various types of substitute and or additional or alternative steps, procedures, and the order for such steps and procedures. Accordingly, even though only few variations of the present methodology and system are described herein, it is to be understood that the practice of such additional modifications and variations and the equivalents thereof, are within the spirit and scope of this application. The corresponding structures, materials, acts, and equivalents of all methods, means, and steps plus function elements in the claims below are intended to include any structure, material, or acts for performing the functions in combination with other claimed elements as specifically claimed.

We claim:

1. A method for determining a patient radiation and diagnostic study score (10) associated with a series of past diagnostic radiologic tests associated with a patient, and treating the patient to manage the risk of cancer associated with future radiologic testing, comprising the steps of:
 a) accessing, by at least one score processor, a database (100) and retrieving data indicative of a plurality of a patient's past radiologic tests (200) during a scoring period, wherein the plurality of past radiologic tests (200) includes at least two different past radiologic tests;
 b) associating, by the at least one score processor, a measure of radiation with each of the plurality of the patient's past radiologic tests (200) from the scoring period;

c) forming, by the at least one score processor, a lifetime attributable risk (400) for each of the plurality of the patient's past radiologic tests (200) from the scoring period, and creating a total lifetime attributable risk (400) for the scoring period;

d) transforming, by the at least one score processor, the total lifetime attributable risk (400) for the scoring period into a scaled lifetime attributable risk (410) for the scoring period by comparing the total lifetime attributable risk (400) for the scoring period with general population radiologic test data, wherein the scaled lifetime attributable risk (410) indicates a measure of the total lifetime attributable risk (400) relative to the general population;

e) creating, by the at least one score processor, the patient radiation and diagnostic study score (10) from the scaled lifetime attributable risk (410) to display on a visual media; and f) treating the patient and directing future radiologic testing at least in part on the patient radiation and diagnostic study score (10).

2. The method of claim 1, wherein the step of forming the lifetime attributable risk (400) for each of the patient's past radiologic tests (200) within the scoring period is further modified by an age adjustment factor (300), wherein the at least one score processor determines the age adjustment factor (300) by analyzing a patient birth date retrieved from the database (100) and a radiologic test date for each radiologic test (200) retrieved from the database (100), and wherein the at least one score processor scales the measure of radiation for each radiologic test (200) by the age adjustment factor (300) for each radiologic test (200) to form the lifetime attributable risk (400) for each radiologic test (200).

3. The method of claim 1, wherein the step of comparing the total lifetime attributable risk (400) for the scoring period with general population radiologic test data, further includes the step of scaling the general population radiologic test data so that the total lifetime attributable risk (400) of approximately unity is associated with a predetermined scaled lifetime attributable risk (410).

4. The method of claim 3, wherein the predetermined scaled lifetime attributable risk (410) associated with the total lifetime attributable risk (400) of approximately unity is approximately 50.

5. The method of claim 1, wherein the step of creating, by the at least one score processor, the patient radiation and diagnostic study score (10) from the scaled lifetime attributable risk (410) to display on a visual media, further includes the step of determining a recent study indicator (500) indicative of the number of radiologic tests (200) performed within a recent indicator time period (510) of no more than one year and including the recent study indicator (500) as a single digit in the patient radiation and diagnostic study score (10).

6. The method of claim 1, wherein the measures of radiation are measures of ionizing radiation.

7. The method of claim 1, further including the steps of creating, by the at least one score processor, a score alert if the patient has the radiation and diagnostic study score (10) is above a predetermined score alert value (600), and treating the patient and directing future radiologic testing at least, in part on the score alert.

8. The method of claim 7, further including the steps of creating, by the at least one score processor, an indicator alert if the patient has the recent study indicator (500) is above a predetermined recent study alert value (520), and treating the patient and directing future radiologic testing at least in part on the indicator alert.

9. A method for determining a patient radiation and diagnostic study score (10) associated with a series of past diagnostic radiologic tests associated with a patient, comprising the steps of:

a) accessing, by at least one score processor, a database (100) and retrieving data indicative of a patient's past radiologic tests (200) during a scoring period;

b) associating, by the at least one score processor, a measure of radiation with each of the patient's past radiologic tests (200) from the scoring period;

c) associating, by the at least one score processor, a previous study factor (800) for each radiologic test (200) from the scoring period that has been performed 2 or more times;

d) associating, by the at least one score processor, a time decay element (900) for each radiologic test (200) from the scoring period that has been performed 2 or more times;

e) forming, by the at least one score processor, a test specific usage metric (1000) for each of the patient's past radiologic tests (200) from the scoring period, wherein the at least one score processor scales the previous study factor (800) for each radiologic test (200) by the time decay element (900) for each radiologic test (200) to form the test specific usage metric (1000) for each radiologic test (200), and using the test specific usage metric (1000) for each radiologic test (200) to create a total usage metric (1000) for the scoring period;

f) transforming; by the at least one score processor, the total usage metric (1000) for the scoring period into a scaled usage metric (1010) for the scoring period by comparing the total usage metric (1000) for the scoring period with general population radiologic test data, wherein the scaled usage metric (1010) indicates a measure of the total usage metric (1000) relative to the general population;

g) creating, by the at least one score processor, the patient radiation and diagnostic study score (10) from the scaled usage metric (1010) and a scaled usage weighting factor (1020), and displaying the patient radiation and diagnostic study score (10) on a visual media; and h) treating the patient and directing future radiologic testing at least in part on the patient radiation and diagnostic study score (10) to manage the risk of cancer associated with radiologic tests.

10. The method of claim 9, further including the steps of:

a) forming, by the at least one score processor, a lifetime attributable risk (400) for each of the patient's past radiologic tests (200) from the scoring period, and creating a total lifetime attributable risk (400) for the scoring period;

b) transforming, by the at least one score processor, the total lifetime attributable risk (400) for the scoring period into a scaled lifetime attributable risk (410) for the scoring period by comparing the total lifetime attributable risk (400) for the scoring period with general population radiologic test data, wherein the scaled lifetime attributable risk (410) indicates a measure of the total lifetime attributable risk (400) relative to the general population; and c) wherein the step of creating, by the at least one score processor, the patient radiation and diagnostic study score (10) includes the scaled lifetime attributable risk (410) and a scaled LAR weighting factor (420).

11. The method of claim 10, wherein the scaled LAR weighting factor (420) ranges from 0.0 to 1.0, and the scaled usage weighting factor (1020) ranges from 0.0 to 1.0.

12. The method of claim 10, wherein the step of forming the lifetime attributable risk (400) for each of the patient's past radiologic tests (200) within the scoring period is further modified by an age adjustment factor (300), wherein the at least one score processor determines the age adjustment factor (300) by analyzing a patient birth date retrieved from the database (100) and a radiologic test date for each radiologic test (200) retrieved from the database (100), and wherein the at least one score processor scales the measure of radiation for each radiologic test (200) by the age adjustment factor (300) for each radiologic test (200) to form the lifetime attributable risk (400) for each radiologic test (200).

13. The method of claim 9, further including the steps of:
   a) associating, by the at least one score processor, a resolution metric (1100) with at least each of the patient's past radiologic tests (200) that are not associated with ionizing radiation, from the scoring period, and using each test specific resolution metric (1100) to create a total resolution metric (1100) for the scoring period;
   b) transforming, by the at least one score processor, the total resolution metric (1100) for the scoring period into a scaled resolution metric (1110) for the scoring period by comparing the total resolution metric (1100) for the scoring period with general population radiologic test data, wherein the scaled resolution metric (1110) indicates a measure of the total resolution metric (1100) relative to the general population; and
   c) wherein the step of creating, by the at least one score processor, the patient radiation and diagnostic study score (10) includes the scaled resolution metric (1110) and a scaled resolution weighting factor (1120).

14. The method of claim 9, further including the steps of:
   a) associating, by the at least one score processor, a resolution metric (1100) with at least each of the patient's past radiologic tests (200) that are not associated with ionizing radiation, from the scoring period, and using each test specific resolution metric (1100) to create a total resolution metric (1100) for the scoring period;
   b) transforming, by the at least one score processor, the total resolution metric (1100) for the scoring period into a scaled resolution metric (1110) for the scoring period by comparing the total resolution metric (1100) for the scoring period with general population radiologic test data, wherein the scaled resolution metric (1110) indicates a measure of the total resolution metric (1100) relative to the general population; and
   c) wherein the step of creating, by the at least one score processor, the patient radiation and diagnostic study score (10) includes the scaled resolution metric (1110) and a scaled resolution weighting factor (1120).

15. A method for determining a patient radiation and diagnostic study score (10) associated with a series of past diagnostic radiologic tests associated with a patient, and treating the patient to manage the risk of cancer associated with future radiologic testing, comprising the steps of:
   a) accessing, by at least one score processor, a database (100) and retrieving data indicative of a plurality of a patient's past radiologic tests (200) during a scoring period, wherein the plurality of past radiologic tests (200) includes at least two different past radiologic tests;
   b) associating, by the at least one score processor, a resolution metric (1100) with at least each of the plurality of the patient's past radiologic tests (200) that are not associated with ionizing radiation, from the scoring period, and using each test specific resolution metric (1100) to create a total resolution metric (1100) for the scoring period;
   c) transforming, by the at least one score processor, the total resolution metric (1100) for the scoring period into a scaled resolution metric (1110) for the scoring period by comparing the total resolution metric (1100) for the scoring period with general population radiologic test data, wherein the scaled resolution metric (1110) indicates a measure of the total resolution metric (1100) relative to the general population;
   d) creating, by the at least one score processor, the patient radiation and diagnostic study score (10) from the scaled resolution metric (1110) to display on a visual media; and
   e) treating the patient and directing future radiologic testing at least in part on the patient radiation and diagnostic study score (10).

16. The method of claim 15, wherein the step of associating, by the at least one score processor, the resolution metric (1100) with at least each of the patient's past radiologic tests (200) that are not associated with ionizing radiation, from the scoring period, further includes the step of associating a resolution metric (1100) with every radiological test (200) from the scoring period.

17. The method of claim 15, wherein the step of creating, by the at least one score processor, the patient radiation and diagnostic study score (10) from the scaled resolution metric (1110) to display on a visual media, further includes the step of determining a recent study indicator (500) indicative of the number of radiologic tests (200) performed within a recent indicator time period (510) of no more than one year and including the recent study indicator (500) as a single digit in the patient radiation and diagnostic study score (10).

18. The method of claim 15, further including the steps of creating, by the at least one score processor, a score alert if the patient has the radiation and diagnostic study score (10) is above a predetermined score alert value (600), and treating the patient and directing future radiologic testing at least in part on the score alert.

19. The method of claim 18, further including the steps of creating, by the at least one score processor, an indicator alert if the patient has the recent study indicator (500) is above a predetermined recent study alert value (520), and treating the patient and directing future radiologic testing at least in part on the indicator alert.

* * * * *